United States Patent
Ovsyshcher et al.

(10) Patent No.: US 7,781,402 B2
(45) Date of Patent: Aug. 24, 2010

(54) METHODS AND IMPLANTABLE DEVICES FOR TREATING SUPRAVENTRICULAR ARRHYTHMIAS

(75) Inventors: Eli Ovsyshcher, Beer Sheba (IL); Ilya A. Fleidervish, Beer Sheba (IL); Yuri Goldberg, Beer Sheba (IL); Vladimir Zeldets, Beer Sheba (IL); Dan Gelvan, Doar-Na HaEla (IL)

(73) Assignee: Closed Loop Therapies Ltd., Beer-Sheva (IL)

( * ) Notice: Subject to any disclaimer, the term of this patent is extended or adjusted under 35 U.S.C. 154(b) by 1075 days.

(21) Appl. No.: 11/246,165

(22) Filed: Oct. 11, 2005

(65) Prior Publication Data

US 2006/0079941 A1 Apr. 13, 2006

Related U.S. Application Data

(60) Provisional application No. 60/617,067, filed on Oct. 12, 2004, provisional application No. 60/710,611, filed on Aug. 24, 2005.

(51) Int. Cl.
*A61K 38/00* (2006.01)
*A61N 1/00* (2006.01)

(52) U.S. Cl. .................. 514/12; 607/2; 607/3; 607/5; 607/9; 607/14; 604/20

(58) Field of Classification Search ................... 604/20; 607/3
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,508,702 A | 4/1985 | Hsiao |
| 4,666,828 A | 5/1987 | Gusella |
| 4,683,202 A | 7/1987 | Mullis |
| 4,801,531 A | 1/1989 | Frossard |
| 4,866,046 A | 9/1989 | Amer |
| 4,879,219 A | 11/1989 | Wands et al. |
| 4,978,338 A | 12/1990 | Melsky et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,527,344 A | 6/1996 | Arzbaecher et al. |
| 5,575,770 A | 11/1996 | Melsky et al. |
| 5,704,910 A | 1/1998 | Humes |
| 5,736,528 A | 4/1998 | Belardinelli et al. |
| 5,911,704 A | 6/1999 | Humes |
| 6,342,250 B1 | 1/2002 | Masters |
| 6,414,018 B1 * | 7/2002 | Duhaylongsod ............ 514/478 |
| 6,444,217 B1 | 9/2002 | Kwok et al. |
| 6,453,195 B1 | 9/2002 | Thompson |
| 6,497,699 B1 | 12/2002 | Ludvig et al. |
| 6,511,500 B1 | 1/2003 | Rahme |
| 6,537,974 B2 | 3/2003 | Wolff |
| 6,541,021 B1 | 4/2003 | Johnson et al. |
| 6,572,605 B1 | 6/2003 | Humes |
| 6,635,049 B1 | 10/2003 | Robinson et al. |
| 6,668,190 B2 | 12/2003 | Iezzi et al. |
| 6,689,373 B2 | 2/2004 | Johnson et al. |
| 6,716,196 B2 | 4/2004 | Lesh et al. |
| 6,716,208 B2 | 4/2004 | Humes |
| 6,728,574 B2 | 4/2004 | Ujhelyi et al. |
| 6,835,194 B2 | 12/2004 | Johnson et al. |
| 6,973,350 B1 | 12/2005 | Levine et al. |
| 2003/0032998 A1 | 2/2003 | Altman |
| 2003/0130616 A1 | 7/2003 | Steil et al. |

FOREIGN PATENT DOCUMENTS

WO  WO 2006/040765  4/2006

OTHER PUBLICATIONS

Rahme et al. "Effect of Autonomic Neurotransmitters on Excitable Gap Composition in Canine Atrial Flutter", Can. J. Physiol. Pharmacol., 79: 13-17, 2001.
Lemola K. et al Pulmonary Vein Region Ablation in Experimental Vagal Atrial Fibrillation of Pulmonary Veins Versus Autonomic Ganglia Circulation 2008 :117; 470-477.
Li, Gui-Rong et al Acacetin, a Natural Flavone. Selectively Inhibits Human Atrial Repolar Potassium Currents and Prevents Atrial Fibrillation in Dogs . Circulation 2008 :117; 24490-2457.
Aidonidis I. et al Assessment of local atrial repolarization in aporcine acetylcholine model of atrial flutterand fibrilation Acta Cardiol 2009; 64 (1);59-64.
Kovoor P. et al Evaluation of the Role of $I_{KAch}$ in Atrial Fibrillation Using a Mouse Knockout Model Journal of the American College of Cardiology vol. 37, No. 8, 2001.

(Continued)

*Primary Examiner*—Christine J Saoud
*Assistant Examiner*—Jegatheesan Seharaseyon
(74) *Attorney, Agent, or Firm*—Martin Fleit; Paul D. Bianco; Fleit Gibbons Gutman Bongini & Bianco PL

(57) ABSTRACT

A medication, method and device for cardiac treatment are provided, in particular, for treating supraventricular arrhythmias. Specifically, a method is provided for treating supraventricular arrhythmias, using a therapeutically effective amount of a cholinergic receptor agonist, for example, acetylcholine. This device may be part of universal device which provides pacing and defibrillation. In particular, the present invention can be used to treat atrial fibrillation, atrial flutter and atrial tachycardia by a bolus injection of a rapidly hydrolysable cholinergic receptor agonist such as acetylcholine.

21 Claims, 14 Drawing Sheets

OTHER PUBLICATIONS

Loomis T.A. et al Auricular Fibrillation Induced and Maintained in Animals by Acetylcho Vagal Stimulation Circ.Res. 1955; 3-390-396.

Ilya A. Fleidervish, Yuri Goldberg and I. Eli Ovsyshcher, Bolus injection of acetylcholine terminates atrial fibrillation in rats, European Journal of Pharmacology, 2008, 579:326-329.

M.R. Boyett, M.S. Kirby, C.H. Orchard and A. Roberts, The Negative Inotropic Effect of Acetylcholine on Ferret Ventricular Myocardium. Journal of Physiology, 1988, 404:613-635.

Morits Bunemann and Lutz Pott, Down-regulation of A1 adenosine receptors coupled to muscarinic K+ current in cultured guinea-pig atrial myocytes, Journal of Physiology, 1995, 482:81-95.

Chuen-Wang Chiou MD, John N. Eble MD and Douglas P. Zipes MD, Efferent vagal innervation of the canine atria and sinus and atrioventricular nodes, The Third Fat Pad, Circulation. American Heart Association, Inc., 1997, 95:2573-2584.

Alfred E. Cohn, Auricular tachycardia with a consideration of certain differences between the two vagi, Journal of Experimental Medicine, 1912, 15:49-62.

Nathan Dascal, Wolfgang Schreibmayer, Nancy F. Lim, Weizhen Wang, Charles Chavkin, Lisa Dimagno, Cesar Labarca, Brigitte L. Kieffer, Claire Gaveriaux-Ruff, David Trollinger, Henry A. Lester and Norman Davidson, Atrial G protein-activated K+ channel: expression cloning and molecular properties Proc Natl Acad Sci USA, 1993, vol. 90:10235-10239.

D. Dobrev, E. Graf E. Wettwer, H. M. Himmel, O. Hala, C. Doerfel, T. Christ, S. Schuler and U. Ravens, Molecular Basis of Downregulation of G-Protein-Coupled Inward Rectifying K(+) Current (I K,ACh) in Chronic Human Atrial Fibrillation: Decrease in GIRK4 mRNA Correlates With Reduced (I K,ACh) and Muscarinic Receptor-Mediated Shortening of Action Potentials, Circulation, Journal of the American Heart Association, 2001, 104:2551-2557.

H. Dobrzynski, N. C. Janvier, R. Leach, J. B. C. Findlay and M. R. Boyett, Effects of ACh and adenosine mediated by Kir3.1 and Kir3.4 on ferret ventricular cells., Am J Physiol Heart Circ Physiol, 2002, 283:H615-630.

Halina Dobrzynski, David D.R. Marples, Hanny Musa, Tomoko T. Yamanushi, Zaineb Henderson, Yoshiko Takagishi, Haruo Honjo, Itsuo Kodama and Mark R. Boyett, Distribution of the Muscarinic K+ Channel Proteins Kir3.1 and Kir3.4 in the Ventricle, Atrium, and Sinoatrial Node of Heart. J Histochem Cytochem, 2001, 49:1221-1234.

Valentin Fuster, et al., ACC/AHA/ESC guidelines for the management of patients with atrial fibrillation: A report of the American . . . , Journal of the American College of Cardiology, 2001, 38:1231-1266.

H. Criss Hartzell, Adenosine receptors in frog sinus venosus: slow inhibitory potentials produced by adenine compounds and acetylcholine, 1979, J Physiol 293:23-49.

Glenn Kabell, Lewis V. Buchanan, John K. Gibson and Luiz Belardinelli, Effects of adenosine on atrial refractoriness and arrhythmias, Cardiovascular Research, 1994, 28:1385-1389.

Hiroaki Kawano, Ryozo Okada and Katsusuke Yano, Histological study on the distribution of autonomic nerves in the human heart, Heart Vessels, 2003,18:32-39.

Matthew E, Kennedy, Jan Nemee, Shawn Corey, Kevin Wickman and David E. Clapham, GIRK4 confers appropriate processing and cell surface localization to G-protein-gated potassium channels, Journal of Biological Chemistry, 1999, 274:2571-2582.

Shin-Ichi Koumi and Andrew Wasserstrom, Acetylcholine-sensitive muscarinic K+ channels in mammalian ventricular myocytes, American Physiological Society, 1994, 266:H1812-1821.

Pramesh Kovoor MD, Kevin Wickman PHD, Colin T. Maguire, William Pu MD, Josef Gehrmann MD, Charles I. Berul MD and David E. Clapham MD PHD, Evaluation of the role of I(KACh) in atrial fibrillation using a mouse knockout model, Journal of the American College of Cardiology, 2001, 37:2136-2143.

G. Krapivinsky, E. A. Gordon, K. Wickman, B. Velimirovic, L. Krapivinsky and D. E. Clapham, The G-protein-gated atrial K+ channel IKACh is a heteromultimer of two inwardly rectifying K(+)-channel proteins, Nature, 1995, 374:135-141.

Yoshihiro Kubo, Eitan Reuveny, Paul A. Slesinger. Yuh Nung Jan and Lily Y. Jan, Primary structure and functional expression of a rat G-protein-coupled muscarinic potassium channel, Nature, 1993, 364:802-806.

Yoshihisa Kurachi, Toshiaki Nakajima and Tsuneaki Sugimoto, On the mechanism of activation of muscarinic K+ channels by adenosine in isolated atrial cells: involvement of GTP-binding proteins, Pflugers Arch, European Journal of Physiology, 1986, 407:264-274.

Diomedes E. Logothetis, Yoshihisa Kurachi, Jonas Galper, Eva J. Neer and David E. Clapham, The beta gamma subunits of GTP-binding proteins activate the muscarinic K+ channel in heart, Nature, 1987, 325:321-326.

S.O. McMoren, S. M. Harrison, W. J. Zang, X.J. Yu and M.R. Boyett, A direct negative inotropic effect of acetylcholine on rat ventricular myocytes, American Physiological Society, 1993, 265:H1393-1400.

G. K. Moe MD and J. A. Abildskov MD, Atrial fibrillation as a self-sustaining arrhythmia independent of focal discharge. Am Heart J., 1959, 58:59-70.

R. Alan North, Drug receptors and the inhibition of nerve cells, Twelfth Gaddum memorial lecture, Br. J. Pharmacol., 1989, 98:13-28.

I. Eli Ovsyshcher and S. Serge Barold, Drug-Induced Bradycardia:To Pace or Not to Pace? Pacing Clin. Electrophysiol., 2004, 27:1144-7.

Eric N. Prystowsky MD Chair, D. Woodrow Benson Jr. MD PHD, Valentin Fuster MD PHD, Robert G. Hart MD, G. Neal Kay MD, Robert J. Myerburg MD, Gerald V. Naccarelli MD, and D. George Wyse MD PHD, Management of patients with atrial fibrillation. A Statement for Healthcare Professionals. From the Subcommittee on Electrocardiography and Electrophysiology, American Heart Association, Circulation, 1996, 93:1262-1277.

Gernot Schram, Marc Pourrier, Peter Melnyk and Stanley Nattel, Differential Distribution of Cardiac Ion Channel Expression as a Basis for Regional Specialization in Electrical Function, Circulation Research, American Heart Association, 2002, 90:939-950.

Makoto Takano and Akinori Noma, Development of muscarinic potassium current in fetal and neonatal rat heart, American Physiological Society, 1997, 272:H1188-1195.

Hung-Fat Tse and Chu-Pak Lau, Does sinus rhythm beget sinus rhythm? Effects of prompt cardioversion on the frequency and persistence of recurrent atrial fibrillation, Cardiac Electrophysiology Review, 2003, 7:359-365.

Albert L. Waldo M.D., Mechanisms of atrial fibrillation, J Cardiovasc Electrophysiol, 2003, 14:S267-274.

Hien J. J. Wellens, Pulmonary vein ablation in atrial fibrillation: hype or hope? Circulation, American Heart Association, Journal of the American Heart Association, 2000, 102:2562-2564.

Marie-Cecile Wellner-Kienitz, Kirsten Bender, Thomas Meyer, Moritz Bunemann and Lutz Pott, Overexpressed A1 Adenosine Receptors Reduce Activation of Acetylcholine-Sensitive K+ Current by Native Muscarinic M2 Receptors in Rat Atrial Myocytes, Circulation Research, American Heart Association, Journal of the American Heart Association, 2000, 86:643-648.

Kevin Wickman, Grigory Krapivinsky, Shawn Corey, Matt Kennedy, Jan Nemec, Igor Medina and David E. Clapham, Structure, G Protein Activation, and Functional Relevance of the Cardiac G Protein-Gated K+ Channel, IKACh, Ann N Y Acad Sci, 1999, 868:386-398.

D. George Wyse MD PHD and Bernard J. Gersh MBCHB DPHIL, Atrial Fibrillation: A Perspective Thinking Inside and Outside the Box, Circulation, 2004;109:3089-3095.

Z. K. Yang, M. R. Boyett, N. C. Janvier, S. O. McMorn, Z. Shui and F. Karim, Regional differences in the negative inotropic effect of acetylcholine within the canine ventricle, Journal of Physiology, 1996, 492:789-806.

Christian Zemlin PHD, Sergey Mironov PHD and Arkady Pertsov PHD, Delayed success in termination of three-dimensional reentry: role of surface polarization, J. Cardiovasc Electrophysiol, 2003, 14:S257-263.

Brian Olshansky, Interrelationships between the autonomic nervous system and atrial fibrillation, Progress in Cardiovascular Diseases, 2005, 48:57-78.

MF Arnsdorf, Cardiac excitability and antiarrhythmic drugs: a different perspective, J Clin Pharmacol, 1989, 29:395-404.

International Search Report published Mar. 20, 2006 for PCT/IL2005/001076 filed Oct. 11, 2005.

Written Opinion of the International Searching Authority published Apr. 12, 2007 for PCT/IL2005/001076 filed Oct. 11, 2005.

International Preliminary Report on Patentability published Apr. 17, 2007 for PCT/IL2005/001076 filed Oct. 11, 2005.

* cited by examiner

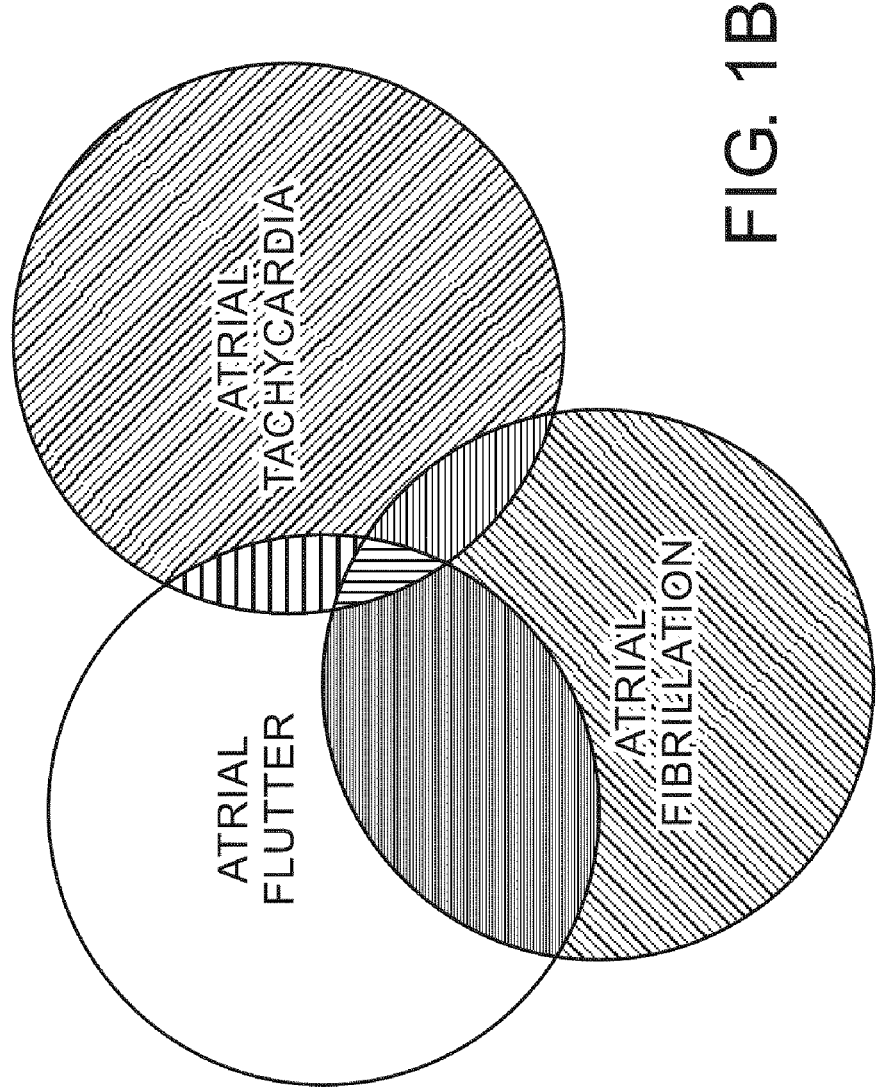

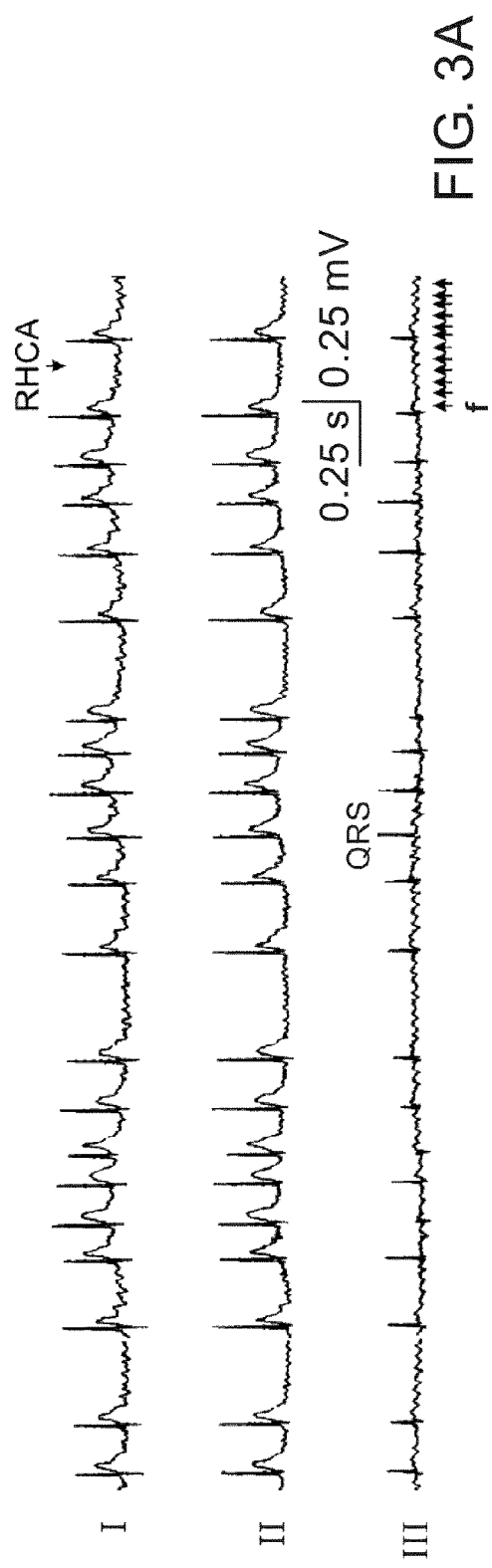
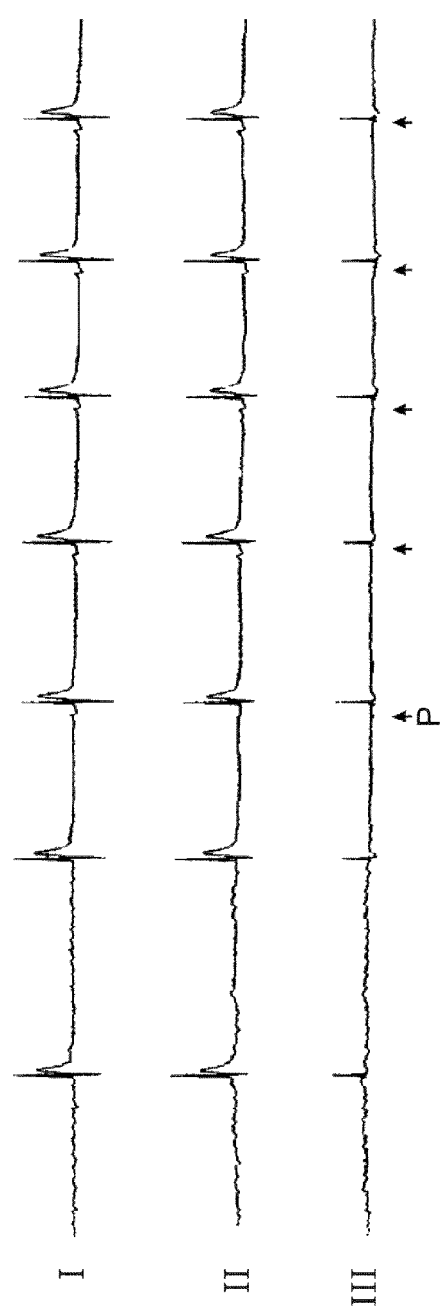
FIG. 3A
FIG. 3B

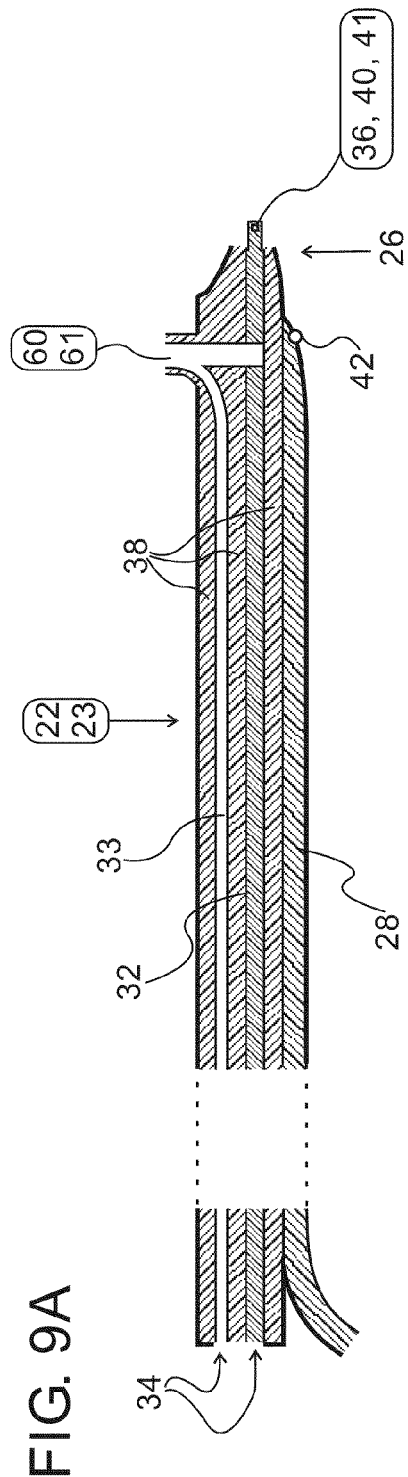
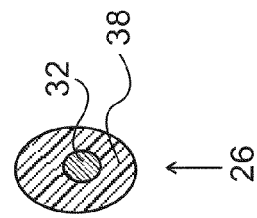
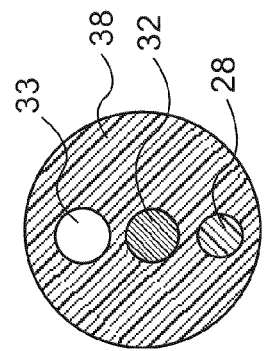
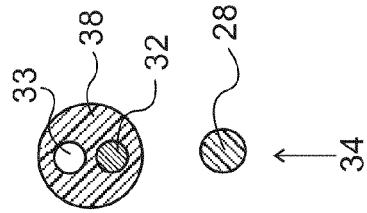

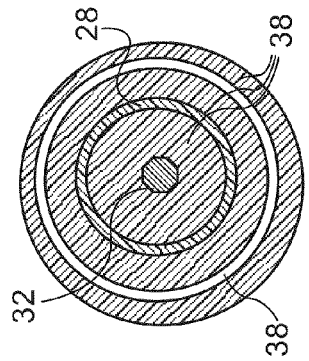
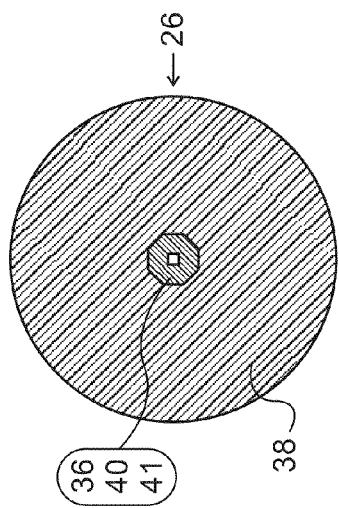
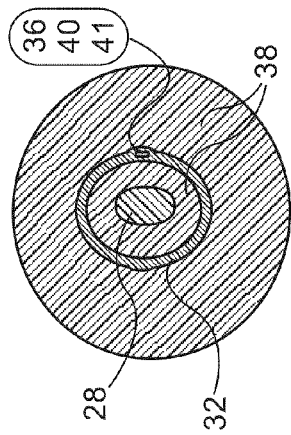
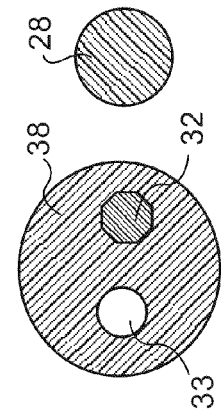
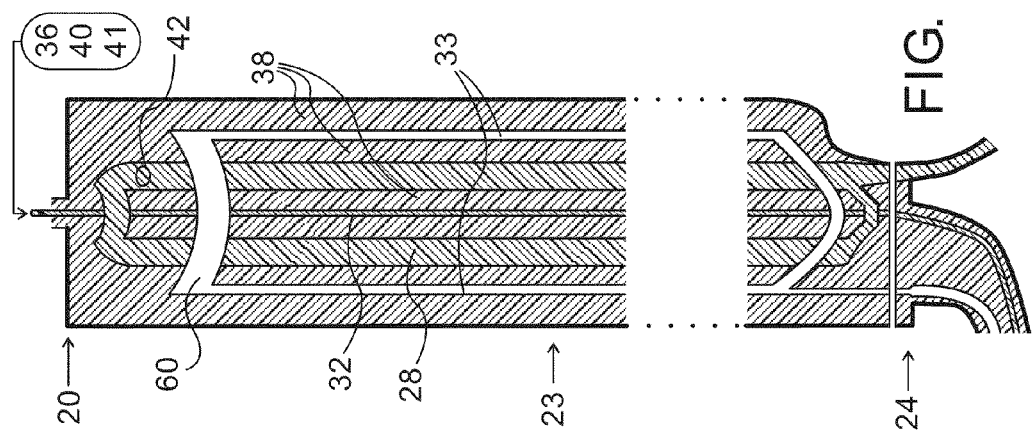

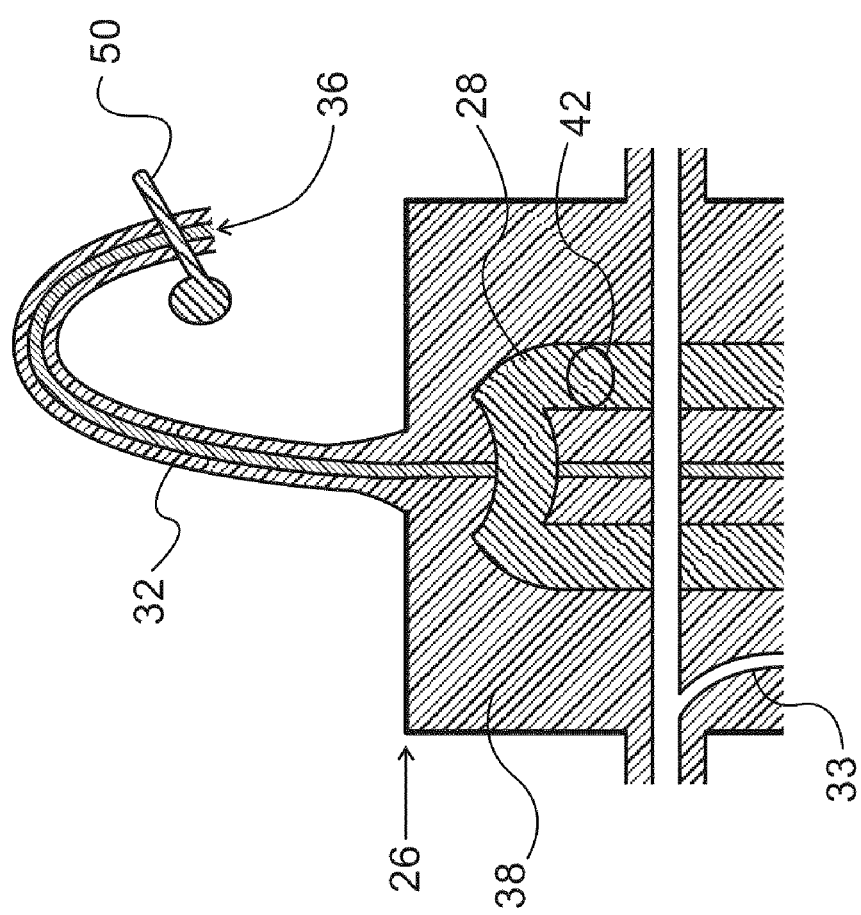

METHODS AND IMPLANTABLE DEVICES FOR TREATING SUPRAVENTRICULAR ARRHYTHMIAS

RELATED APPLICATIONS

The present application claims priority from U.S. Provisional Application No. 60/617,067, filed on Oct. 12, 2004, and U.S. Provisional Patent Application No. 60/710,611, filed on Aug. 24, 2005, the contents of which are herein incorporated by reference.

FIELD AND BACKGROUND OF THE INVENTION

The present invention relates generally to a medication and an implantable device, and in particular, to a medication, method and device for cardiac treatment.

Supraventricular arrhythmias such as atrial tachycardia, atrial flutter, and atrial fibrillation are characterized by rapid and frequently ineffective contraction of the atria which lead to inefficient heart performance. Atrial flutter is characterized by a rapid and regular rhythm of the atria (typically 300 flutter or f-waves/minute) but not the ventricles (typically 150 beats/minute). Atrial fibrillation is characterized by an irregular and usually rapid heart rhythm in which the atria fibrillate more than 300-350 impulses or f-waves per minute while the ventricular rate is in the range of 120-200 beats per minute. During atrial fibrillation, the electrical signals start irregularly and usually from several places in the atria and travel erratically throughout the atria, leading to blood pools and clots which increase the risk of stroke. Approximately 15-25% of all strokes can be attributed to atrial fibrillation. In addition, the cardiac output in atrial fibrillation is only 70-80 percent of normal, leading to shortness of breath and fatigue. In many cases, atrial fibrillation is associated with arterial hypertension as well as structural diseases of the heart or the lung. If untreated, the short paroxysms of atrial fibrillation can transform to persistent or permanent appearance, leading to significant complications such as stroke, cardiomyopathy and heart failure.

To restore normal heart rhythm various antiarrhythmic drugs can be used. These include quinidine, procainamide, disopyramide, flecainide, propafenone, dofetilide, ibutilide, azimilide, amiodarone and β-blockers (especially sotalol). However, such medications are only effective in 30-60% of the cases and usually lose their effectiveness over short period of time. In addition, some drugs have potentially serious side effects. Control of the heart rate can be achieved using β-blockers, calcium channel blockers and digoxin. To reduce the risks of clot formation, anticoagulant and/or antiplatelet drugs such as coumadin (warfarin) and/or aspirin are prescribed. Coumadin reduces the risk of stroke by 60-80% in people with atrial fibrillation.

In cases such drugs are not efficient in restoring sinus rhythm, one of the following procedures may be applied:

I. Electrical cardioversion: To synchronize the heart and restore a normal rhythm, an electrical shock is delivered to the patient's chest wall (sometime intracardially or transesophageal) after administration of a short-acting anesthesia.

II. Catheter ablation: Ablation of the AV node or the right and/or left atrium is performed using soft wires (catheters) which are inserted through the veins (e.g., in the groin) and guided to the heart. In AV ablation, the radiofrequency (RF) energy is delivered through the catheter to destroy the AV node. Because the ablation causes heart block, a permanent pacemaker is further implanted to maintain adequate heart rates. In atrium ablation, the catheters are used to "map" the atrium and to deliver RF energy to ablate or isolate foci that fire or propagate abnormal electrical impulses (e.g., isolation of pulmonary veins in the left atrium, or such ablation procedures as "maze" or "corridor"). The RF energy (as well other sources of energy such as freezing or cryo) produces a scar that blocks any abnormal impulses from propagating within the left, right or both atria, thus preventing atrial fibrillation from occurring.

III Implantable Device Therapy:

a. An implantable cardioverter-defibrillator (ICD) is a device designed to provide automatic conversion of ventricular fibrillation to normal rhythm by electrical shock. Some commercially available ICDs have the capacity to provide atrial electrical shock in addition to the standard ventricular therapy. Wellens et al., describe an implantable atrioverter for the treatment of atrial fibrillation (Wellens H J J, et al., 1998, Circulation, 98: 1651-6). Significant discomfort and often intolerable pain is associated with intracardiac shock therapy by implantable atrioverter resulting in the need for sedation of some patients and refusal to accept the therapy by other. Currently stand alone atrial cardioverter-defibrillators are not available.

b. A permanent pacemaker is a device that sends low energy electrical impulses to the heart muscle to maintain a suitable heart rate. The pacemaker includes a pulse generator (which contains a battery and electronic circuitry) and pacing lead(s) (wires) that deliver the impulses from the pulse generator to the right atrium, right ventricle and, in some cases, the left ventricle through the coronary sinus, and sense the spontaneous heart's electrical activity in atrium and ventricle(s). Although atrium-based pacing is associated with a lower risk of atrial fibrillation and stroke than ventricle-based pacing for patients requiring pacemakers for bradyarrhythmias, the use of pacing as a primary therapy for prevention of recurrent atrial fibrillation as well as for it treatment has not been validated.

c. Implantable devices for drug delivery are designed to monitor and control the release of a drug from the device. These devices are often used for long-term infusion of drugs in patients having chronic diseases such as diabetes mellitus, cancer, spasticity, pain and others. Usually, such pumps comprise a pressurized drug source which can be refilled while the device is implanted. Examples of implantable drug devices are described in U.S. Pat. Nos. 4,978,338, 6,541,021 and 6,689,373, 6,835,194, 6,728,574, 6,716,208, 6,572,605, 5,911,704, 5,704,910, 6,668,190, 6,444,217 and 6,342,250, all of which are fully incorporated herein by reference.

U.S. Pat. No. 6,497,699 to Ludvig et al., entitled "Hybrid neuroprosthesis for the treatment of brain disorders", describes a miniature apparatus for the treatment of brain disorder. The disclosed hybrid system is a combination of electronic and pharmacological devices placed and powered entirely within the human body.

U.S. Pat. No. 6,453,195 to Thompson, describes an externally mounted transdermal drug delivery device, in communication with at least one implantable medical device, designated to deliver pain analgesics prior to shock therapy by an atrial defibrillator. The drug delivery device includes an attachable strip with storage for medications and is epidermally mounted. The medications are released into the bloodstream in response to an indication that the implantable device is about to deliver a shock. The drug delivery device is adapted for use with various drugs. Further, the delivery of drugs could be controlled by the patient to provide a semi-automatic use.

U.S. Pat. No. 5,527,344 to Arzbaecher et al., discloses an implantable apparatus for automatically delivering a defibrillating drug to a patient upon the detection of the onset of atrial fibrillation. In this system, the delivery time is continuously computed and the delivery signal is emitted as function of the monitored level of atrial activity. However, the efficiency of such a device in treating atrial fibrillation was not proven, mainly due to the fact that at present no suitable defibrillating drug for conversion atrial fibrillation to sinus rhythm can be administered via such a device.

IV. Heart surgery: Patients with highly symptomatic paroxysmal, persistent and permanent atrial fibrillation not alleviated by medication or catheter ablation procedures, or have other conditions requiring heart surgery, are candidates for surgical treatment of atrial fibrillation (e.g., "maze" or "corridor" procedures). Surgical operations for atrial fibrillation have been successfully combined with operative correction of a variety of structural cardiac conditions such as valvular, ischemic, or congenital heart disease, although this entails additional risk. The mortality rate of an isolated "maze" operation is about 1%, but mortality is higher when the procedure is combined with other types of operative repair. The morbidity associated with the operation includes consequences common to thoracotomy and cardiopulmonary bypass, as well as a risk of transient or permanent reduction in left and right atrium transport function, and early postoperative atrial tachyarrhythmias. In addition, sinus node dysfunction might require a permanent pacemaker implantation. Currently, surgical operations of cardiac lesions frequently combined with intra-operative catheter ablation of atrial fibrillation.

There is thus a widely recognized need for, and it would be highly advantageous to have, a method, a drug and a device for treating atrial fibrillation devoid of the above limitations.

SUMMARY OF THE INVENTION

According to one aspect of the present invention there is provided a method of treating supraventricular arrhythmias in a subject in need thereof the method comprising: administering to the subject a therapeutically effective amount of a cholinergic receptor agonist, the cholinergic receptor agonist being selected for transiently modulating at least one electrical property of at least a portion of atrial cells thereby treating the supraventricular arrhythmia in the subject.

According to another aspect of the present invention there is provided a use of a cholinergic receptor agonist for the treatment of supraventricular arrhythmias, the cholinergic receptor agonist being selected transiently modulating at least one electrical property of at least a portion of atrial cells.

According to yet another aspect of the present invention there is provided a use of a cholinergic receptor agonist for the manufacture of a medicament identified for the treatment of supraventricular arrhythmias, the cholinergic receptor agonist being selected for transiently modulating at least one electrical property of at least a portion of atrial cells.

According to still another aspect of the present invention there is provided a device comprising a device body adapted for implantation into a body and a sensor for sensing an activity of a heart being in contact with the device body when implanted into the body, the device body housing a reservoir for holding a cholinergic receptor agonist suitable for intracardiac or and/or intravascular administration.

According to an additional aspect of the present invention there is provided a device comprising a device body adapted for implantation into a body, the device body housing a reservoir for holding a cholinergic receptor agonist for administering into or close to a tissue.

According to yet an additional aspect of the present invention there is provided an implantable cardiac treatment device, comprising a reservoir containing a cholinergic receptor agonist and a releasing mechanism for releasing a predetermined dose of the cholinergic receptor agonist in, on or in proximity to a heart.

According to further features in preferred embodiments of the invention described below, the SVA is atrial fibrillation.

According to still further features in the described preferred embodiments the SVA is atrial tachycardia.

According to still further features in the described preferred embodiments the SVA is atrial flutter.

According to still further features in the described preferred embodiments administering is effected by a bolus injection.

According to still further features in the described preferred embodiments the cholinergic receptor agonist is selected capable of modulating at least one electrical property of at least a portion of atrial cells.

According to still further features in the described preferred embodiments the cholinergic receptor agonist is formulated for intravascular, intramuscular and/or intracardiac administration.

According to still further features in the described preferred embodiments the intravascular administration is effected via a vein and/or an artery.

According to still further features in the described preferred embodiments the vein is a peripheral vein, a central vein and/or a coronary sinus.

According to still further features in the described preferred embodiments the central vein is a superior vena cava and/or an inferior vena cava.

According to still further features in the described preferred embodiments the artery is a coronary artery and/or a pulmonary artery.

According to still further features in the described preferred embodiments the intracardiac administration is into a chamber of a heart.

According to still further features in the described preferred embodiments the intracardiac administration is effected via the right atrium, left atrium, right ventricle, and/or left ventricle.

According to still further features in the described preferred embodiments the administration is effected using a catheter, a cannula, a needle, syringe and/or a pump.

According to still further features in the described preferred embodiments the catheter is a part of a pacing lead-catheter.

According to still further features in the described preferred embodiments the catheter comprises a lumen for drug delivery.

According to still further features in the described preferred embodiments the cholinergic receptor agonist is acetylcholine or an acetylcholine salt.

According to still further features in the described preferred embodiments the acetylcholine salt is selected from the group consisting of acetylcholine chloride, acetylcholine bromide, acetylcholine iodide.

According to still further features in the described preferred embodiments the therapeutically effective amount of the cholinergic receptor agonist is selected from a range of 0.001-20 mg per 1 kg body weight.

According to still further features in the described preferred embodiments the therapeutically effective amount of the cholinergic receptor agonist is selected from a range of 0.02-0.4 mg per 1 kg body weight.

According to still further features in the described preferred embodiments the therapeutically effective amount of the cholinergic receptor agonist is selected incapable of modulating the at least one electrical property of ventricular cells.

According to still further features in the described preferred embodiments modulating the at least one electrical property is effected via a cholinergic receptor.

According to still further features in the described preferred embodiments the at least one electrical property is selected from the group consisting of refractoriness, excitability, speed of excitation propagation, focal automaticity, and spatial pattern of excitation.

According to still further features in the described preferred embodiments the therapeutically effective amount of the cholinergic receptor agonist is selected to transiently modulate the at least one electrical property of the at least a portion of the atrial cells for no more than 5 seconds.

According to still further features in the described preferred embodiments the cholinergic receptor is a muscarinic m2 receptor.

According to still further features in the described preferred embodiments the medicament is administered via a bolus injection.

According to still further features in the described preferred embodiments the activity is an electrical activity.

According to still further features in the described preferred embodiments the activity is a mechanical activity.

According to still further features in the described preferred embodiments a housing of the device is sealed.

According to still further features in the described preferred embodiments a seal of the device is formed of a puncturable material.

According to still further features in the described preferred embodiments the puncturable material is selected so as to allow replenishing of said cholinergic receptor agonist in the reservoir.

According to still further features in the described preferred embodiments puncturing the seal is effected using a needle.

According to still further features in the described preferred embodiments, the device further comprising an electrically controlled valve associated with the reservoir, the electrically controlled valve is suitable for controlling a release of the cholinergic receptor agonist.

According to still further features in the described preferred embodiments, the device further comprises a controller selected capable of controlling the electrically controlled valve, the controller being located within the device body.

According to still further features in the described preferred embodiments, the device further comprises a power source for powering the controller, the power source being in electrical communication with the controller.

According to still further features in the described preferred embodiments, the device further comprising a catheter, the catheter having a proximal end at the housing and a distal end positionable in proximity to the tissue, the catheter defining a lumen, the lumen running substantially the length of the catheter and opening into an orifice, wherein the electrically controlled valve controls a release of the medicament into the lumen.

According to still further features in the described preferred embodiments, the device further comprises an electrical lead, the electrical lead running at least substantially the length of the catheter and having a proximal end in electrical communication with the controller, and a distal end associated with the tissue.

According to still further features in the described preferred embodiments the catheter is a part of a pacing lead-catheter.

According to still further features in the described preferred embodiments the sensor is located at the distal end of the electrical lead.

According to still further features in the described preferred embodiments the device is operative as a pacemaker.

According to still further features in the described preferred embodiments the device is operative as an ICD.

According to still further features in the described preferred embodiments the sensor is an electrode.

According to still further features in the described preferred embodiments the electrode is hooked or screwed to engage with a muscle of the heart.

According to still further features in the described preferred embodiments the sensor is a transducer.

According to still further features in the described preferred embodiments the orifice is in a right side of the heart.

According to still further features in the described preferred embodiments the orifice is in a vein leading to a right side of the heart.

According to still further features in the described preferred embodiments the tissue is a heart.

According to still further features in the described preferred embodiments, the device further comprises a sensor for sensing supraventricular arrhythmias of the heart.

According to still further features in the described preferred embodiments, wherein the sensor communicates with the releasing mechanism for releasing the predetermined dose of the cholinergic receptor agonist in, on or in proximity to the heart when the supraventricular arrhythmias of the heart are sensed by the sensor.

The present invention successfully addresses the shortcomings of the presently known configurations by providing a medication, method and device for cardiac treatment, in particular, for treating supraventricular arrhythmias. Specifically, a method is provided for treating supraventricular arrhythmias, using a therapeutically effective amount of a cholinergic receptor agonist, for example, acetylcholine. Additionally a device is provided, for sensing and evaluating the heart rhythm, and for pacing and (or) administering a therapeutically effective amount of the cholinergic receptor agonist. In particular, the present invention can be used to treat supraventricular arrhythmias including atrial fibrillation, atrial flutter and atrial tachycardia, by a bolus injection of a rapidly hydrolysable cholinergic receptor agonist such as acetylcholine.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1b—a schematic illustration depicting the common and different features of atrial fibrillation, atrial flutter and atrial tachycardia, all belong to the family of supraventricular arrhythmias (adapted from Wyse and Gersh, 2004). These arrhythmias are closely interrelated, and the individual forms often coexist in the same patient. Although the present invention focuses primarily on atrial fibrillation, many of the points made with regard to atrial fibrillation apply to these other arrhythmias to varying degrees;

FIG. 2a—The three traces (marked I, II and III) represent ECG recording from the three standard leads. Note the effect of RHCA injection through the tail vein in correcting atrial tachycardia following 2.6 seconds. FIG. 2b—The two traces (I and I cont.) represent ECG recording from standard lead I over an extended time period of 10 seconds. Note that following 0.5 second from the administration of the RHCA, the atrial tachycardia was terminated. After short period (1.25 seconds) of cardiac arrest two escape nodal beats appeared and the sinus node activity recovered (appeared P-waves) with high degrees of AV block. Following about 4.5 seconds, the AV conduction completely recovered;

FIGS. 3a-b—are ECG recordings of the three standard leads (I, II, and III) from a rat after the induction of atrial fibrillation and the suppression of atrial fibrillation by RHCA administration via the right ventricular cavity. FIG. 3b represents a continuation over a time scale of the ECG recording of FIG. 3a. Note the variable f-f and R-R intervals characterizing atrial fibrillation prior to RHCA administration. Following 1.5 seconds of a bolus injection of 0.1 ml of 0.2 mg/ml acetylcholine (dosage 0.04 mg/kg body weight), atrial fibrillation was converted into sinus rhythm; transient sinus bradycardia was maximal immediately following the injection and disappeared completely within 20 seconds (not shown);

FIGS. 9a-d—schematically illustrates an isometric view, and cross sectional views of integrated lead-catheter, in accordance with one embodiment of the present invention;

FIGS. 10a-e—schematically illustrates an isometric view and cross-sectional views at different parts of the integrated lead-catheter, in accordance with another embodiment of the present invention;

FIG. 11—schematically illustrates the distal end of the integrated lead-catheter, in accordance with yet another embodiment of the present invention;

DESCRIPTION OF THE PREFERRED EMBODIMENTS

Figure 1A:
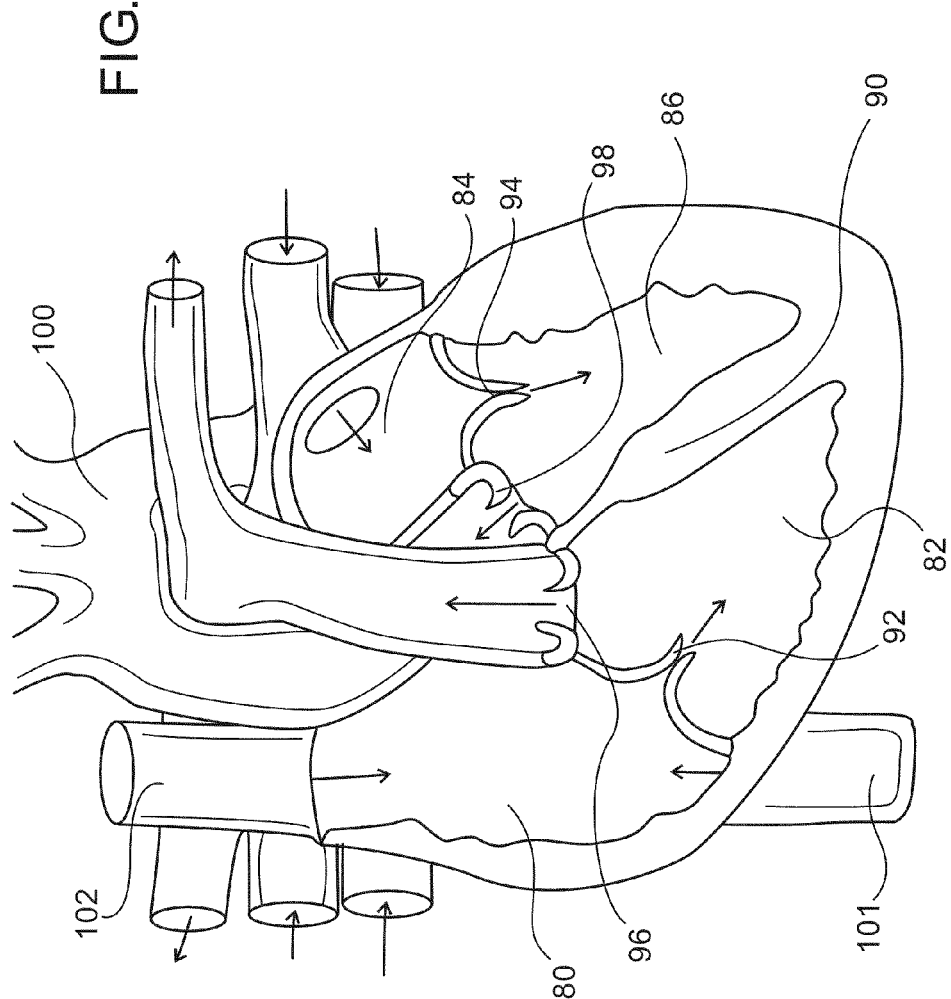
FIG. 1a—depicts the structure of the heart. A heart 5, having a right atrium 80, a right ventricle 82, a left atrium 84 and a left ventricle 86. A septum 90, separating between the right and left ventricles, a tricuspid valve 92, enabling a blood flow from the right atrium 80 to the right ventricle 82, a mitral valve 94, enabling a blood flow from the left atrium 84 to the left ventricle 86, a pulmonary valve 96, enabling a blood flow exit the right ventricle 82 towards the lungs (not shown in figure), an aortic valve 98, enabling a blood flow from the LV 86 to an aorta 100, and the superior vena cava 102 and inferior vena cava 101 bringing blood back from a body to the right atrium 80.

The present invention is of a medication, method and device for cardiac treatment, in particular, for treating supraventricular arrhythmias. Specifically, a method is provided for treating supraventricular arrhythmias, using a therapeutically effective amount of a cholinergic receptor agonist, for example, and acetylcholine. Additionally a device is provided, for sensing and evaluating cardiac arrhythmias, and for pacing and/or administering the therapeutically effective amount of the cholinergic receptor agonist. In particular, the present invention can be used to treat atrial fibrillation, atrial tachycardia and atrial flutter, by a bolus injection of a rapidly hydrolysable cholinergic receptor agonist such as acetylcholine.

The principles and operation of the medication, method and device for cardiac treatment, according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Supraventricular arrhythmias such as atrial fibrillation, atrial flutter and atrial tachycardia are characterized by rapid and frequently ineffective contraction of the atria and inefficient heart function. Generally, subjects suffering from paroxysms of supraventricular arrhythmias may exhibit inefficient heart performance and experience tiredness, weakness, dizziness, shortness of breath, pressure or discomfort in the chest. In atrial fibrillation, for example, the rapid and uncoordinated depolarization and ineffective contraction of the atria often leading to the formation of blood clots in the left atrium and thus increase the risk of stroke in the subject. Thus, if untreated, atrial fibrillation can lead to a life-threatening condition.

Common treatment regimens of atrial fibrillation include the use of antiarrhythmic drugs such as quinidine, procainamide, disopyramide, flecainide, propafenone, dofetilide, ibutilide, azimilide, amiodarone and β-blockers (especially sotalol). Recently, a novel mixed ion channel antagonist, RSD1235, has demonstrated its effectiveness to convert recent-onset atrial fibrillation to sinus rhythm in a large, international, phase 3, randomized, placebo-controlled clinical trial (Roy D, et al., The ACT I Investigators. RSD1235 for conversion of atrial fibrillation. The Phase III Atrial Arrhythmia Conversion Trial. Program and abstracts from the Heart Rhythm 2005 26th Annual Scientific Sessions; May 4-7, 2005; New Orleans, La.; Roy D, et al., CRAFT Investigators. A randomized, controlled trial of RSD1235, a novel antiarrhythmic agent, in the treatment of recent onset atrial fibrillation. J. Am. Coll. Cardiol. 2004; 44:2355-2361). However, such drugs are effective in only 30-60% of the cases and may lose their effectiveness over time. When the antiarrhythmic drugs fail to control the arrhythmia, an electrical cardioversion (e.g., an electric shock) can be used to restore a normal rhythm. However, although frequently efficient in restoring normal heart rhythm, such a procedure requires anesthesia involving sometime serious complications. Other treatment regimens include ablation of the atrioventricular node followed by implantation of a permanent pacemaker, or ablation of the atrial tissue. Alternatively, an implantable cardioverter-defibrillator can be used to restore normal rhythm during an atrial fibrillation episode.

Figure 2A:
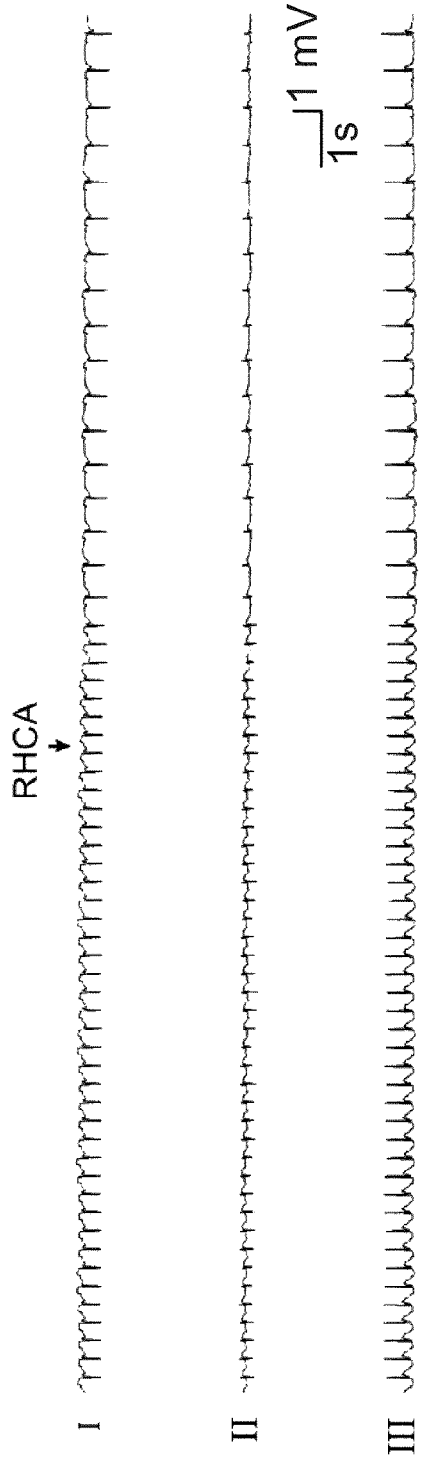
FIGS. 2a-b—are ECG recordings from a rat after the induction of atrial tachycardia and the termination of atrial tachycardia following the injection of acetylcholine, the rapidly hydrolysable cholinergic receptor agonist (RHCA), into the tail vein (FIG. 2a) or the right ventricular cavity (FIG. 2b).
Figure 2B:
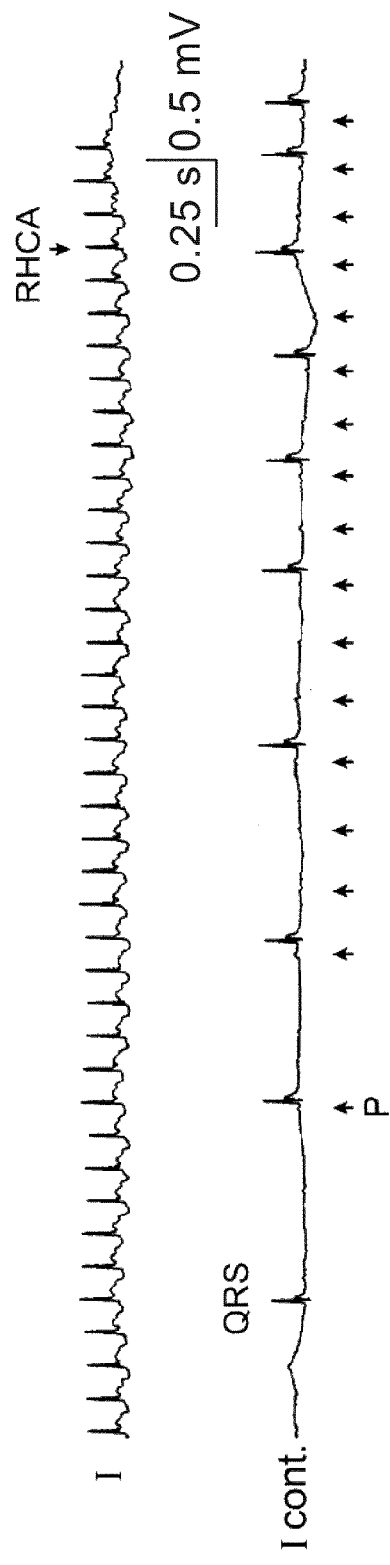

While reducing the present invention to practice, the present inventors have uncovered that a bolus injection of a relatively low dose of acetylcholine (ACh) can terminate supraventricular arrhythmia. As is shown in FIGS. 2a-b and is described in Example 1 of the Examples section which follows, a bolus injection of 0.02 or 0.2 mg/kg body weight of ACh via the right ventricular cavity or the tail vein of a rat, respectively, terminated atrial tachycardia within 0.5-15 seconds. Moreover, a bolus injection of ACh (0.04-0.2 mg/kg body weight) terminated atrial fibrillation within 0.5-15 seconds and restored normal rhythm within additional 1-5 seconds of ACh administration (FIGS. 3a-b and 5, Example 2 of the Examples section which follows). These results therefore suggest the use of a bolus administration of ACh or any other rapidly hydrolysable cholinergic receptor agonist for treating supraventricular arrhythmias such as atrial fibrillation, atrial flutter and atrial tachycardia.

The teachings of the present invention are in sharp contrast to prior art studies which demonstrate a detrimental effect of ACh on atrial flutter and atrial fibrillation and therefore teach away using ACh for the treatment of these arrhythmias. Thus, series of classical works from Moe's and Zipes's laboratories show that an increase in vagal modulation promotes the stability of atrial fibrillation, because vagal stimulation shortens the atrial refractory period and decreases the wavelength of the reentrant circuits. Furthermore, increased dispersion of atrial refractoriness contributes to the vagal effects on perpetuation of atrial fibrillation (Allessie et al., 1958, Am J Physiol. 194:406-410; Zipes et al., 1974, Cardiovasc. Res. 8: 647-655). Continuous infusion of low doses of acetylcholine (2 µg/minute into a 29-45 kg body weight) reverses the effect of the antiarrhythmic drug d,1-sotalol, shortens the effective refractory period and the length of the atrial flutter cycle and increases the excitable gap duration (U.S. Pat. No. 6,511,500 to Marc M. Rahme; Marc M. Rahme, et al., 2001, Can. J. Physiol. Pharmacol. 79: 13-17). Similarly, vagal stimulation shortens atrial refractoriness suggesting increased risk for arrhythmias (Prystowsky, E. N., et al., 1983, Am. J. Cardiol. 51: 96-100). In addition, intravenous injection of acetylcholine (ACh) in both wild type (WT) and M1 cholinergic receptor knockout (M1-KO) mice was found to induce arrhythmia, i.e., caused atrioventricular conduction block and induced atrial fibrillation or flutter (Hardouin, S. N., et al., 2002, JPET 301: 129-137).

Thus, according to one aspect of the present invention there is provided a method of treating supraventricular arrhythmias in a subject. The method is effected by administering to a subject in need thereof a therapeutically effective amount of a cholinergic receptor agonist, the cholinergic receptor agonist being selected transiently modulating an electrical property of at least a portion of atrial cells thereby treating the supraventricular arrhythmia in the subject.

The term "treating" refers to inhibiting or arresting the development of a disease, disorder or condition and/or causing the reduction, remission, or regression of a disease, disorder or condition associated with supraventricular arrhythmias. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" includes mammals, preferably, human beings of both sexes. Preferably, this term encompasses an individual who is at risk of developing supraventricular arrhythmias and/or suffers from supraventricular arrhythmias, such as an individual who suffers from hypertension, coronary artery disease, lung disease(s), valvular lesion(s) and/or heart failure. Preferably, the subject of the present invention can be an individual who suffers from supraventricular arrhythmias.

As used herein the phrase "supraventricular arrhythmias" refers to any arrhythmia present in the atria. The term "arrhythmia" as used herein refers to any ectopic atrial rhythm (ectopic i.e., not including normal sinus rhythm) such as rapid beats, slow beats or a combination thereof. The term encompasses atrial beats with variable intervals of the P or f (fibrillation/flutter) waves or abnormal pattern of P waves. It will be appreciated that such atrial arrhythmias are often associated with uncoordinated depolarization in the atria and/or with irregular conduction of electrical signal from the atria to the ventricles via the atrioventricular (AV) node resulting in inefficient heart function.

Preferably, the phrase "supraventricular arrhythmias" encompasses atrial tachycardia, atrial fibrillation and atrial flutter. In humans, atrial tachycardia is characterized by a rapid rate of depolarization in the atria, typically resulting in 160-200 beats per minute; atrial fibrillation is characterized by an irregular atrial depolarization resulting in a very rapid atrial rhythm of about 350-600 impulses per minute; atrial flutter is characterized by a rapid but regular atrial rhythm of about 250-350 (typically 300) beats per minutes.

As used herein the phrase "cholinergic receptor agonist" refers to any molecule capable of binding to, inducing, stimulating, and/or activating a cholinergic receptor.

The phrase "cholinergic receptor" refers to both nicotinic acetylcholine receptors composed of various α (e.g., α1-α10), β (e.g., β1-β4), γ, δ and ε subunits (InterPro Accession No. for the family of Nic/ace_receptor proteins IPR002394) and/or muscarinic acetylcholine receptors such as the M1, M2, M3, M4 and M5 subunits (InterPro Accession No. for the family of MusAcC_receptor proteins IPR001065). According to one embodiment of the present invention, the cholinergic receptor of the present invention is a muscarinic cholinergic receptor such as the muscarinic M2 receptor-G protein-coupled K+ channels Kir3.1 and Kir 3.4 (GenBank Accession No. P08172; SwissProt ACM2_HUMAN) present in the atrial myocardium. For example, the cholinergic receptor agonist used by the present invention can be the neurotransmitter acetylcholine itself and/or various analogues and/or derivatives thereof.

According to one preferred embodiment, the cholinergic receptor agonist used by the present invention is acetylcholine. The acetylcholine used by the present invention can be the acetylcholine per se [i.e., $(CH_3)_3N^+CH_2CH_2OCOCH_3$], acetylcholine in a salt formulation (i.e., acetylcholine salt) (available from various suppliers such as Sigma, St Louis, Mo., USA; Merck), a chemical derivative(s) and/or analogue thereof. Acetylcholine derivatives (e.g., dichlorophosphate-acetylcholine) are designed to prolong the stability and/or half life of acetylcholine. It will be appreciated that such a derivative should be rapidly hydrolysable yet exhibiting a longer half-life than acetylcholine itself.

Non-limiting examples of acetylcholine salts include, but are not limited to, acetylcholine iodide (Fluka Cat. No. 01030), acetylcholine chloride (Sigma Cat. Nos. A6625, A2661; Biochemika Cat. No. 01018) and acetylcholine bromide (Sigma Cat. No. A6500). Preferably, the acetylcholine used by the present invention is acetylcholine chloride (Sigma Cat. No. A6625).

Non-limiting examples of acetylcholine analogues include carbachol, phospholine iodide, methacholine iodide, phosphorus oxychloride, bethanecol, methacholine, pilocarpine and cytidyl diphosphocholine.

According to another preferred embodiment, the cholinergic receptor agonist used by the present invention is an agonist of acetylcholine-induced activity. For example, such a molecule can be a secondary or tertiary messenger molecule which acts downstream or upstream of the cholinergic receptor of the present invention.

It will be appreciated that formulations of acetylcholine are generally stable at −20° C. in a form of powder, lyophilized or as a concentrated solution (e.g., in the molar range) in aqueous solution such as, water, PBS or saline. It will be appreciated that once diluted to low concentrations such as in the micromolar range and in the presence of higher temperatures, such as in physiological temperature (e.g., 37° C.), acetylcholine becomes less stable and those of skills in the art are capable of determining the conditions (e.g., storage concentration, temperature and pH, etc.) required for maintaining acetylcholine stable. For example, the acetylcholine used by the present invention can be prepared in an appropriate buffer, in high concentrations such as in the molar range and when needed, can be diluted, in an appropriate buffer, to millimolar or micromolar ranges such as those used for injection into the rats (e.g., 0.1 mg/ml which is equivalent to 550 μM; see Examples 1 and 2 of the Examples section which follows).

It will be appreciated that the cholinergic signal induced by the cholinergic receptor agonist is capable of disabling pacemaking in the SA node and conductivity in the AV node (due to the activation of the same metabolic and ionic pathways which are responsible for atrial fibrillation termination). In order to restore such activities (e.g., pacemaking and conductivity), as well as the normal pattern of signal propagation at the AV node and atrial myocardium, the cholinergic receptor agonist used by the present invention preferably exhibits a short-term effect. Such a short-term effect can be achieved, for example, by a rapidly hydrolysable cholinergic receptor agonist, which is degraded within seconds by a suitable hydrolyzing enzyme [e.g., acetylcholinesterase (AChE) or butyrylcholinesterase (BChE)]. Additionally or alternatively, such a short-term effect can be achieved by administering an acetylcholine analogue followed by the administration of the appropriate hydrolyzing enzyme.

Preferably, the effect of the cholinergic receptor agonist of the present invention lasts for 1-60 seconds following administration, more preferably, 1-50 seconds, more preferably, 2-40 seconds, more preferably, 2-30 seconds, more preferably, 2-20 seconds, more preferably, 2-10 seconds, even more preferably, 2-5 seconds following administration.

According to preferred embodiment of the present invention the cholinergic receptor agonist used by the present invention is selected such that it exerts its effect on atrial cells (i.e., terminating supraventricular arrhythmias) without causing an undesired side effect on other cells, such as lung cells. In addition, such an agonist should be stable enough to reach the target cells (e.g., atrial cells) from the site of administration (e.g., from the device which is further described hereinbelow or from the blood circulation). Thus, the type, formulation and concentration of the cholinergic receptor agonist used by the method of the present invention should be adjusted to the agonist half-life and stability.

According to the method of the present invention, the cholinergic receptor agonist used by the present invention is selected capable of transiently modulating an electrical property of at least a portion of atrial cells, preferably via a cholinergic receptor.

As used herein, the phrase "transiently modulating an electrical property" refers to temporally (i.e., for a short time as described hereinbelow) varying or changing the refractoriness (i.e., the state, synchronization and/or duration of the refractory period of a cell), excitability (i.e., the ability of cells to generate and propagate action potentials), speed of excitation propagation (i.e., the velocity in which action potentials propagate), focal automaticity (i.e., the ability of cardiac cells and their groups to generate depolarizing post-potentials under normal and abnormal circumstances), spatial pattern of excitation and refractoriness of at least a portion of atrial cells.

For example, as described in Examples 1 and 2 of the Examples section which follows, administration of acetylcholine resulted in a modulation of the frequency of P (FIGS. 2a-b) and f (FIGS. 3a-b and 5) waves during atrial tachycardia and atrial fibrillation, respectively. Thus, FIGS. 2 and 3 show that administration of acetylcholine rapidly terminates the arrhythmia either by stopping the abnormal focal automaticity or by converting the abnormal spatial pattern of propagation of excitation and refractoriness (e.g., reentry) into the normal one, or by both. The cellular mechanisms of these effects relate to the transient activation of potassium conductance which, by hyperpolarizing and shunting the cellular membrane, prevents focal automaticity and transiently turns atrial cells to less excitable or even inexcitable.

According to preferred embodiments of the present invention, the transient modulation is effected for a time period in the range of 0.2 millisecond (ms) to 60 seconds, more preferably, for a time period in the range of 0.5 ms to 50 seconds, more preferably, for a time period in the range of 1 to 40 seconds, more preferably, for a time period in the range of 2 to 30 seconds, more preferably, for a time period in the range of 2 to 20 seconds, more preferably, for a time period in the range of 2 to 10 seconds, even more preferably, for a time period in the range of 2 to 5 seconds.

Due to the large gradient in the density of the muscarinic $K^+$ channel density between atria and ventricles, there is a relatively wide range of a muscarinic agonist concentrations which maximally or almost maximally affect the atrial and nodal tissues but exhibit no effect on excitability or contraction of the ventricular myocardium.

It will be appreciated that the concentration of the cholinergic receptor agonist used by the present invention should be selected such that it is capable of modulating the electrical properties of atrial cells without substantially modulating the electrical properties of ventricular cells. Such a concentration can be determined using in vitro and ex vivo studies.

For example, in vitro studies utilizing rat myocardial cells demonstrated that a concentration of $10^{-9}$ to $3 \times 10^{-8}$ M acetylcholine causes nearly maximal effects in rat atrial cells but exhibits no effect on the electrical properties and inotropy of ventricular cells (McMorn et al., 1993 Am. J. Physiol. 265: H1393-1400).

The cholinergic receptor agonist of the present invention can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cholinergic receptor agonist (e.g., acetylcholine) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include intravascular administration [via a vein (e.g., superior or inferior vena cava, or another central or peripheral vein) or an artery], rectal, intraperitoneal, sublingual, percutaneous, intestinal or parenteral delivery, including intramuscular, intrathecal, intracardiac administration and/or into a coronary artery. As used herein, the phrase "intracardiac administration" refers to any administration into a heart chamber, including a direct intraventricular administration (e.g., to the right or the left ventricle), administration into the right atrium or the left atrium. It will be appreciated that administration into the left atrium can be effected by introducing a specially developed catheter via the atrial septum into the left atrium. Such a catheter can be introduced through a puncture in the atrial septum or by using an open patent foramen ovale. It will be appreciated that such a catheter can be attached to an implantable device as is further described hereinbelow.

According to preferred embodiments of the present invention, administration is effected by intravascular administration (e.g., through a peripheral vein, a central vein, the coronary sinus and/or the pulmonary artery) and/or intracardiac administration, preferably, into the right atrium, or the right ventricle.

Administration can be effected using a catheter, syringe, pump, and/or other devices, for the administration of medications intravascularly or directly into the heart.

Pharmaceutical compositions of the present invention may be manufactured by processes well known in the art, e.g., by means of conventional mixing and dissolving processes.

According to embodiments of the present invention a method for manufacturing a medicament for the treatment of SVA is disclosed. The aforementioned method comprises steps of a. selecting a cholinergic receptor agonist capable of transiently modulating at least one electrical property of at least a portion of atrial cells and b. incorporating said cholinergic receptor agonist in said medicament.

Pharmaceutical compositions for use in accordance with the present invention thus may be formulated in a conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer (e.g., 0.9% NaCl).

The pharmaceutical composition described herein may be formulated for parenteral administration, e.g., by bolus injection. Formulations for injection may be presented in unit dosage form, e.g., in ampoules or in multidose containers with optionally, an added preservative. The compositions may be suspensions or solutions in aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate water based injection suspensions. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose.

As used herein the phrase "therapeutically effective amount" means an amount of active ingredients (i.e., a cholinergic receptor agonist such as acetylcholine) effective to prevent, alleviate or ameliorate symptoms and complications of pathology (i.e., supraventricular arrhythmias, e.g., atrial tachycardia, atrial fibrillation and/or atrial flutter) and prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro, cell culture or in vivo assays. For example, a dose can be formulated in animal models (e.g., rats, dogs or pigs) to achieve a desired concentration or titer. Such information can be used to more accurately determine useful doses in humans.

Toxicity and therapeutic efficacy of the cholinergic receptor agonist described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the cardiac cells (e.g., in the atria) with levels of the cholinergic receptor agonist which are sufficient to terminate and treat the supraventricular arrhythmias, i.e., minimal effective concentration, (MEC). It will be appreciated that the MEC can vary depending on the type of supraventricular arrhythmias to be treated, weight of the subject and the mode of administration. For example, as is shown in Examples 1 and 2 of the Examples section which follows, when administered via the right ventricular cavity a dose of 0.02 mg/kg body weight was capable of treating atrial tachycardia and a dose of 0.04 mg/kg body weight was capable of treating atrial fibrillation. The MEC will vary for each preparation, but can be estimated from in vitro data. Detection assays can be used to determine plasma concentrations.

Depending on the severity and responsiveness of the condition to be treated, dosing can be of a single or a plurality of administrations, until cure is effected or diminution of the disease state is achieved. It will be appreciated that since the cholinergic receptor agonist used by the present invention is rapidly hydrolysable and therefore does not accumulate in the body, the dosage units may be administered many times with short time intervals of several minutes or less.

The amount of a composition to be administered will, of course, be dependent on the subject being treated, the severity of the affliction, the manner of administration, the judgment of the prescribing physician, etc.

According to preferred embodiments of the present invention, the therapeutically effective amount of acetylcholine is selected from a range of 0.001-20 mg per kilogram (kg) body weight, more preferably, from a range of 0.005-10 mg per kg body weight, more preferably, from a range of 0.01-10 mg per kg body weight, more preferably, from a range of 0.01-5 mg per kg body weight, more preferably, from a range of 0.02-1 mg per body weight, more preferably, from a range of 0.02-0.4 mg per kg body weight.

For example, for treating of atrial fibrillation or atrial tachycardia in a subject weighing 70 kg, a bolus injection of acetylcholine (e.g., acetylcholine chloride in 0.9% sodium chloride) in the range of 1.4-28 mg can be used. For intracardiac administration, such a dose can be prepared in a volume of 0.1 ml (14-280 mg/ml); for intravenous administration, such a dose can be prepared in a volume of 1 ml (1.4-28 mg/ml).

According to embodiments of the present invention, a method for manufacturing a medicament for the treatment of SVA is disclosed. The method comprises additional steps of preparing the medicament for administering as a bolus injection.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by FDA for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

While further reducing the present invention to practice, the present inventors have constructed an implantable device capable of sensing an electrical activity of a tissue (e.g., supraventricular arrhythmias in the heart) and administering a medicament (e.g., a cholinergic receptor agonist such as described hereinabove) in response to such electrical activity.

Thus, according to another aspect there is provided a device comprising a device body adapted for implantation into a body and a sensor for sensing an activity of a tissue being in contact with the device body when implanted into the body, the device body housing a reservoir for holding a medicament.

The activity of the tissue according to this aspect of the present invention can be an electrical activity or a mechanical activity.

As used herein the phrase "electrical activity of a tissue" refers to an electrical activity (e.g., current, voltage, frequency) which modifies the electrical property of the tissue as described hereinabove. A non-limiting example of such electrical activity is represented by the P and f waves or one of the waves of the QRS complex.

A mechanical activity of a tissue can be for example, a contraction and relaxation of atria and ventricles.

The device of the present invention can be implanted in or in close proximity to, any tissue having a measurable activity (e.g., electrical property) such as nervous tissue (e.g., brain, spinal cord), muscular tissue (e.g., heart, smooth or skeletal muscle), and endo- and exocrine tissue. According to one preferred embodiment, the electrical activity which is sensed by the device of the present invention is of the heart tissue, preferably electrical activity associated with the right atrium or right ventricle.

Figure 7:
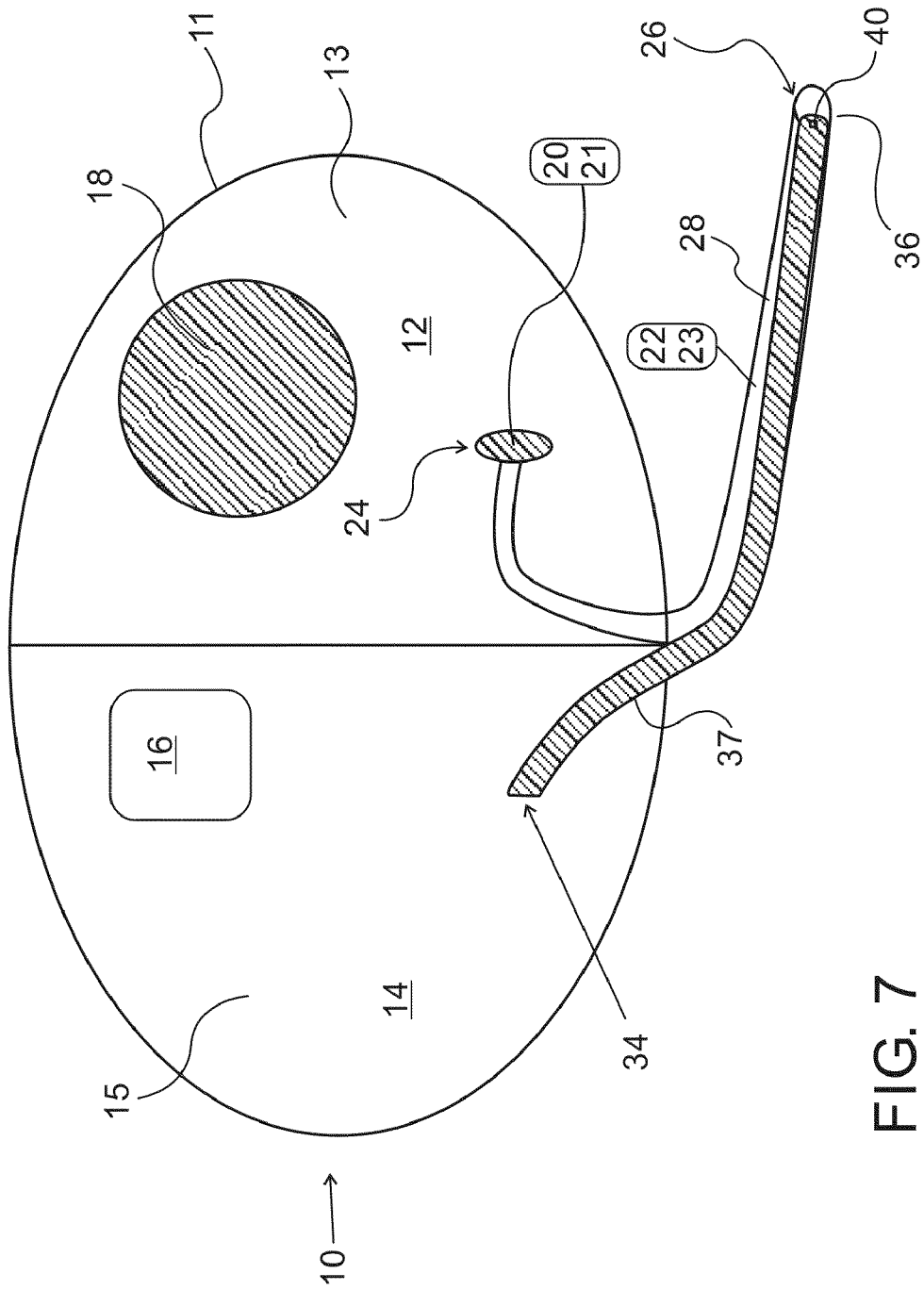
FIG. 7—schematically illustrates the structure of a cardiac device for treating supraventricular arrhythmias, in accordance with the present invention.

Referring further to the drawings, FIG. 7 schematically illustrates the structure of an implantable device 10 which is configured suitable for treating heart arrhythmia disorders in accordance with the teachings of the present invention.

Figure 12A:
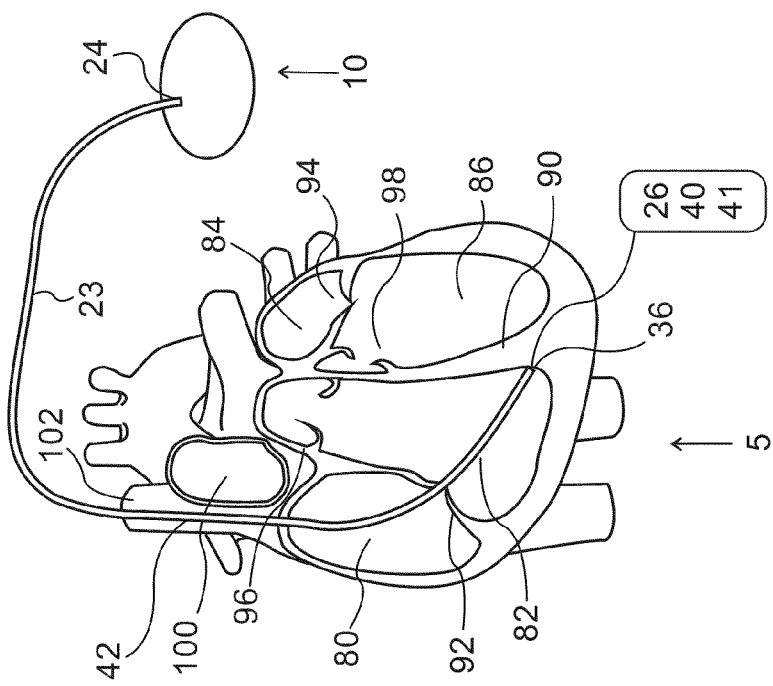
FIGS. 12a-b—schematically illustrates the placement of the cardiac device within the body, with the distal end of the catheter in the right hand side of the heart, in accordance with two embodiments of the present invention.
Figure 12B:
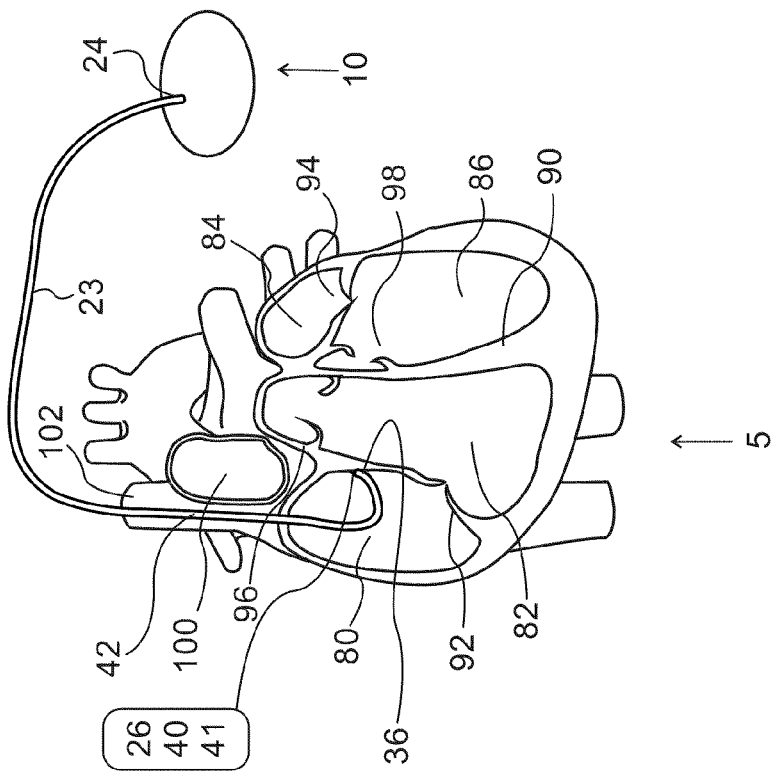

Cardiac device 10 includes a sealed housing 11, adapted for implantation in a body 7 (as illustrated hereinbelow, in conjunction with FIG. 8a). Device 10 includes a catheter 22 connected to sealed housing 11, for delivering a medication 13 stored in a medication reservoir 12 that is located within housing 11, to a targeted tissue, in this case heart tissue, preferably into right ventricle 82 or right atrium (as shown in FIGS. 12a-b). Device 10 also includes a sensor 40 which is capable of sensing cardiac activity. Sensor 40 can form a part of housing 11 or be connected thereto. Device 10 preferably also includes a control unit 14, located within housing 11. Control unit 14 is electrically connected to a proximal end 34 of an electrical lead 37 which is in turn connected to sensor 40 at a distal end 36. Control unit 14 functions converting sensor 40 signals into control commands for controlling release of medication 13 from medication reservoir 12.

Sealed housing 11 is fabricated from titanium or any other biocompatible material suitable for in-tissue implantation and is preferably designed as a flat member having at least two sections, one section being a medication reservoir 12 which is hollow for containing a medication 13 suitable for cardiac treatment, as prescribed, and the second section for containing control unit 14 and a power supply unit 16 for powering sensor 40 and control unit 14. The length of sealed housing 11 is selected from a range of 2-15 cm [preferably 5-10 cm], while a width thereof is selected from a range of 2-10 cm. The volume of reservoir 12 is selected from a range of 1-100 milliliter [preferably 5-30 ml].

Figure 8B:
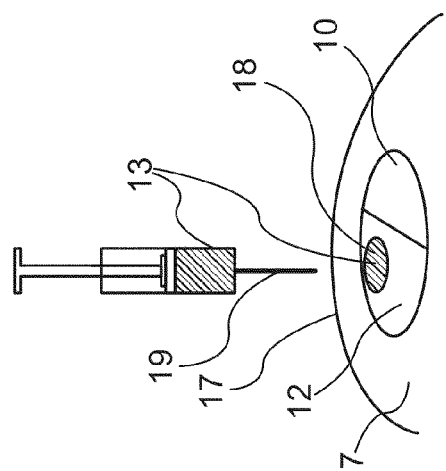
FIGS. 8a-b—schematically illustrates the placement of the cardiac device in a body and a way of replenishing the medication reservoir with medication, in accordance with a preferred embodiment of the present invention.

Medication reservoir 12 has an internal volume of about 1-100 milliliters and is fabricated from a suitable material for containing medication 13 which may include one type of medication or any combination of medicaments suitable for treatment. Medication 13 preferably includes a cholinergic receptor agonist such as acetylcholine and optionally any other type of medication suitable for use with the present invention. Medication reservoir 12 includes a seal 18, formed of a puncturable material (i.e., a material which can be punctured) which will reseal when a needle 19 (shown in FIG. 8b hereinbelow) is withdrawn, for replenishing medication reservoir 12 using e.g., a needle 19, (FIG. 8b). An electrically controlled valve 20, possibly associated with a pump 21, allows the release of medication 13, from reservoir 12. As used herein the phrase "associated with a pump" refers to either a direct or an indirect contact between the electrically controlled valve and the pump. For example, an indirect contact may be via any signaling route (e.g., radio frequency). Valve 20 is responsive to commands of control unit 14. It should be noted that although device 10 is described herein as having a single reservoir 12, multiple reservoir device configurations which are capable of separately providing to heart (or any other) tissue several types of medications are envisaged. For example, a device 10 having 2 reservoirs, one for holding a cholinergic receptor agonist and the other an antagonist thereof can be used to more finely control heart rhythm fluctuations. Another example is of device 10 having one reservoir containing a drug and a second reservoir for holding a dissolving liquid such as 0.9% NaCl solution. Such a multi-reservoir configuration can also be used to provide medication which otherwise cannot be stored in the same reservoir (e.g., different pH requirements and the like).

Sensor 40 can be a plurality of sensors 40 wherein sensor(s) 40 can be any type of sensor capable of sensing electrical, mechanical and hemodynamic activity of the heart, e.g., heart depolarization, heart contraction, blood flow, blood pressure and the like. Sensor(s) 40 is/are preferably connected to control unit 14 through a lead 37 (e.g., an electrical lead) which communicates sensor 40 signal to control unit 14 and optionally also communicates signals from control unit 14 to sensor 40 (which can also function as an electrode for pacing). It is appreciated that sensor 40 may be either a part of lead 37 or connected to distal end 36 of lead 37. Further description of various types of sensors is provided hereinunder (FIGS. 9a-11). Sensor 40 is connected to control unit 14 which receives signal information from sensor 40 and converts such signal information into commands for controlling opening and closing valve 20 of reservoir 12. Furthermore, control unit 14 may also include a pacemaker 15 and thus be capable of single chamber, dual chamber and biventricular pacing i.e., conventional dual chamber pacing or right ventricular pacing combined with left ventricular pacing via distal veins of coronary sinus (CS) for cardiac resynchronization therapy (CRT); McAlister F A, et al. Systematic Review: Cardiac Resynchronization in Patients with Symptomatic Heart Failure. *Ann Intern Med.* 2004; 141:381-390, and the like, and/or be capable of functioning as a defibrillator or (e.g., function as a universal implantable cardiac device including a pacemaker with all modes of pacing and defibrillator with all kinds of defibrillation) as described hereinbelow, in conjunction with FIGS. 9a-11. Pacemaker 15 component of control unit 14 can be assumed by, for example, a Medtronic AT500 system. Alternatively, pacemaker 15 may be any of the Integrity AFx from St. Jude Medical or Insignia Plus from Guidant, or another pacemaker, as known. Furthermore pacemaker 15 may be part of an ICD such as Medtronic's Marquis or Guidant's Vitality or another ICD, as known.

Power supply unit 16 for powering control unit 12 and sensor 40 can be any battery utilizable in implantable devices. Alternatively, power supply unit 16 may be a micro-generator, for example, as taught in PCT publication WO 2004/032788 (PCT/IL2003/000808), whose disclosure is incorporated herein by reference.

As is mentioned hereinabove, catheter 22 of device 10 functions in conducting the medication from reservoir 12 to the tissue site targeted. As such, catheter 22 has a proximal end 24 connected to medication reservoir 12, and a distal end 26 that is configured suitable for delivering the medication to a tissue, in this case, a heart 5 tissue (as seen in FIG. 8a). Preferably, the distal end of catheter 22 is positionable in proximity to the tissue. As used herein the term "proximity" refers to being in a cavity defined by the tissue, for example, if the tissue in which the medication is released is a blood vessel (artery or vein) the cavity is a lumen of such a blood vessel. On the other hand, if the tissue in which the medication is released is a heart chamber, then the cavity is an atrium or a ventricle. A length of catheter 22 is selected from a range of 1-70 cm while a width thereof is selected from a range of 2-8 mm. Catheter 22 is preferably integrated with lead 37 of sensor 40. Such an integrated lead-catheter 23 (i.e., a catheter integrated with a lead) that includes electrical lead 37 and defines a lumen 28 that runs substantially the length of integrated lead-catheter 23, is further described in conjunction with FIGS. 9a-11 hereinbelow. It is appreciated that catheter 22 and lead 37 may be separated for administering medication to one location while sensing a different location. For example, lead 37 is connected to the right atria while catheter 22 delivers medication to IVC 101. Catheter 22 or integrated lead-catheter 23 is made of any appropriate bio-compatible material, including, for example, polymers or metals or any combination thereof.

According to preferred embodiments of the present invention, the integrated lead-catheter is a pacing lead-catheter. As used herein, the phrase "pacing lead-catheter" refers to a lead-catheter (as described hereinabove) capable of sending an electrical signal to a tissue (e.g., a heart) and/or delivering a medicament to the tissue (e.g., the cholinergic receptor agonist of the present invention).

According to preferred embodiments of the present invention, the lead, pacing lead or the lead-catheter described hereinabove can function as a sensor for sensing the electrical activity of the heart.

It will be appreciated that following the administration of the cholinergic receptor agonist which is capable of modulating the electrical properties of the atrial cells, the device is preferably functioning as a pacemaker (using e.g., pacemaker 15) to restore normal heart rhythm (if needed).

Figure 8A:
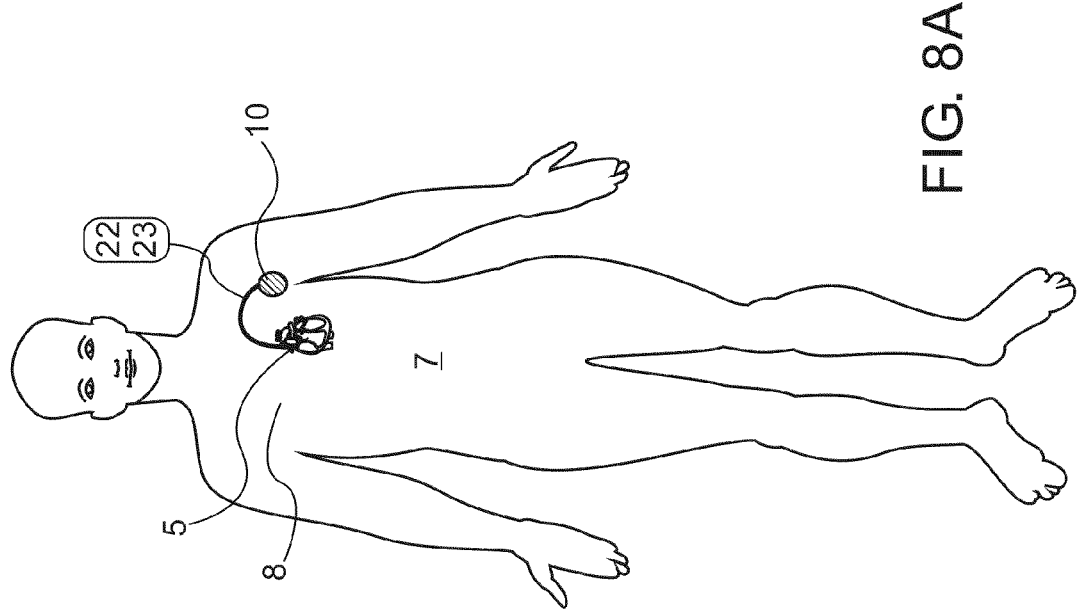

Reference is now made to FIGS. 8a-b which schematically illustrate the placement of cardiac device 10 in a body 7, for treating a heart 5, while also illustrate replenishment of medication reservoir 12 with medication 13, in accordance with a preferred embodiment of the present invention.

FIG. 8a schematically illustrates placement of cardiac device 10 in a body 7 (e.g. subcutaneous in a chest 8), in a manner similar to placement of any permanent pacemaker or implantable cardioverter defibrillator (ICD). Additionally FIG. 8a illustrates establishment of a connection between integrated lead-catheter 23 of cardiac device 10 and heart 5, providing an electrical connection, for transferring electrical signals between heart 5 and cardiac device 10, and providing lumen 28 (see FIGS. 7, 9a-11) within which medication 13 may flow from medication reservoir 12 to heart 5.

FIG. 8b schematically illustrates the use of needle 19 for puncturing seal 18 through skin 17 and replenishing medication reservoir 12 with medication 13.

FIGS. 9a-d schematically illustrates an isometric view, and cross sectional views of integrated lead-catheter 23 described above. Integrated lead-catheter 23 provides both electrical and fluid connections between cardiac device 10 and heart 5 (as shown in FIG. 8a). Integrated lead-catheter 23 includes a cathode 32, an anode 33, and an electrical insulating material 38. Additionally, integrated lead-catheter 23 includes a lumen 28 through which medication 13 are transferred from medication reservoir 12 to heart 5. Furthermore, cathode 32, running substantially the length of integrated lead-catheter 23, has a proximal end 34 and a distal end 36. Proximal end 34 is in electrical contact with control unit 14 (as shown in FIG. 7), and distal end 36 is in contact with heart 5 (as shown in FIGS. 12a-b). Distal end 36 may be formed as an electrode 41, for sensing any heart functions, for example, electrical. Additionally, electrode 41 may be used for electrical stimulation of heart 5, when cardiac device 10 includes pacemaker 15 (as seen in FIG. 7 hereinabove) or ICD. Additionally, anode 33, which is in electrical contact with control unit 14 on one side runs along integrated lead-catheter 23 until a second point 60 which is formed as a ring 61 close to distal end 26 of integrated lead-catheter 23, could be free-floating in the cavity of the heart chamber or in contact with internal wall (endocardium) of heart 5. It is to be noted that cathode 32 and anode 33 used for sensing and pacing as described herein above, together with control and power units, 14 and 16, serve as a bipolar lead. It is also possible to have second point of contact 60, for creating a potential difference with electrode 41, at housing 11 itself, or elsewhere in body 7 for example subcutaneously, in the left side of the subclavicular area (describing a unipolar lead).

As shown in FIGS. 1a, 7, and 9a) additionally or alternatively, sensor 40, (e.g. a piezoelectric sensor) may be placed at or near distal end 36, for example, for sensing heart beat. Cathode 32 and anode 33 are enclosed within an electrical insulating material 38, as is commonly practiced. Opening of valve 20 (shown in FIG. 7) mobilizes medication 13 from medication reservoir 12 (shown in FIG. 7) to heart 5 (shown in FIG. 8a) through lumen 28 and an orifice 42 which is located close to distal end 26 of integrated lead-catheter 23, near sensor 40 and (or) electrode 41, or anywhere else along the length of integrated lead-catheter 23. Orifice 42 located along the length of integrated lead-catheter 23 may be useful in cases where medication 13 in superior vena cava 102 or in the atrial or ventricular cavities is desired and yet placement of sensor 40, or electrode 41, against the heart muscles, for example, of right atrium 80, or right ventricle 82 is preferred (shown in FIGS. 12a and 12b).

FIGS. 10a-e schematically illustrates an isometric view (10a) and cross-sectional views at different parts of integrated lead-catheter 23, in accordance with another embodiment of the present invention. In the embodiment described here, cathode 32 runs substantially the length of integrated lead-catheter 23 and anode 33 has a cylindrical shape. Additionally, integrated lead-catheter 23 comprises a ring shaped lumen 28 confined between anode 33 and cathode 32 for mobilizing medication 13 from medication reservoir 12 to heart 5 (as shown in FIG. 8a). Preferably, cylindrical shaped anode 33 has an electrical insulating layer 38 internally and externally. Furthermore, cathode 32 has sensor 40 and (or) electrode 41 at distal end 26 of integrated lead-catheter 23 for sensing heart 5. For example, sensor 40 may be a transducer 40. Orifice 42 may be located close to distal end 26 of integrated lead-catheter 23, near sensor 40 and (or) electrode 41, or anywhere else along the length of integrated lead-catheter 23.

FIG. 10e illustrates an additional embodiment of catheter 23 of device 10 of the present invention. In this embodiment cathode 32 has a cross section which is shaped as a ring. Additionally, lumen 28 may have a cylindrical shape internal to cathode 32 running substantially the length of integrated lead-catheter 23. Furthermore, orifice 42 from which medication 13 leaves lumen 28 may be located at distal end 26 of integrated lead-catheter 23 (as shown in FIG. 10e) or close to distal end 26 of integrated lead-catheter 23, near sensor 40 and (or) electrode 41, or anywhere else along the length of integrated lead-catheter 23.

Reference is now made to FIG. 11, which schematically illustrates distal end 26 of integrated lead-catheter 23, in accordance with yet another embodiment of the present invention. Accordingly, distal end 36 of cathode 32 is configured to engage a muscle of the heart 5 via a screw 50.

FIGS. 12a-b, schematically illustrate the placement of cardiac device 10 in body 7 (as shown in FIG. 8a), with distal end 26 of integrated lead-catheter 23 in the right hand side of heart 5, in accordance with a preferred embodiment of the present invention.

As seen in FIG. 12a, distal end 26 of integrated lead-catheter 23, with sensor 40 and (or) electrode 41 are placed in contact with the internal wall (endocardium) of right atrium 80, while orifice 42 is located in superior vena cava 102, so that medication 13 is released to superior vena cava 102. Alternatively, orifice 42 may be located in right atrium 80 or right ventricle 82, so that medication 13 is released there.

As seen in FIG. 12b, distal end 26 of integrated lead-catheter 23, with sensor 40 and (or) electrode 41 are placed in contact with the internal wall (endocardium) of right ventricle 82, while orifice 42 may be located in superior vena cava 102, right atrium 80, or right ventricle 82, so that medication 13 is released there. It will be appreciated that other combinations and locations are possible.

Figure 13:
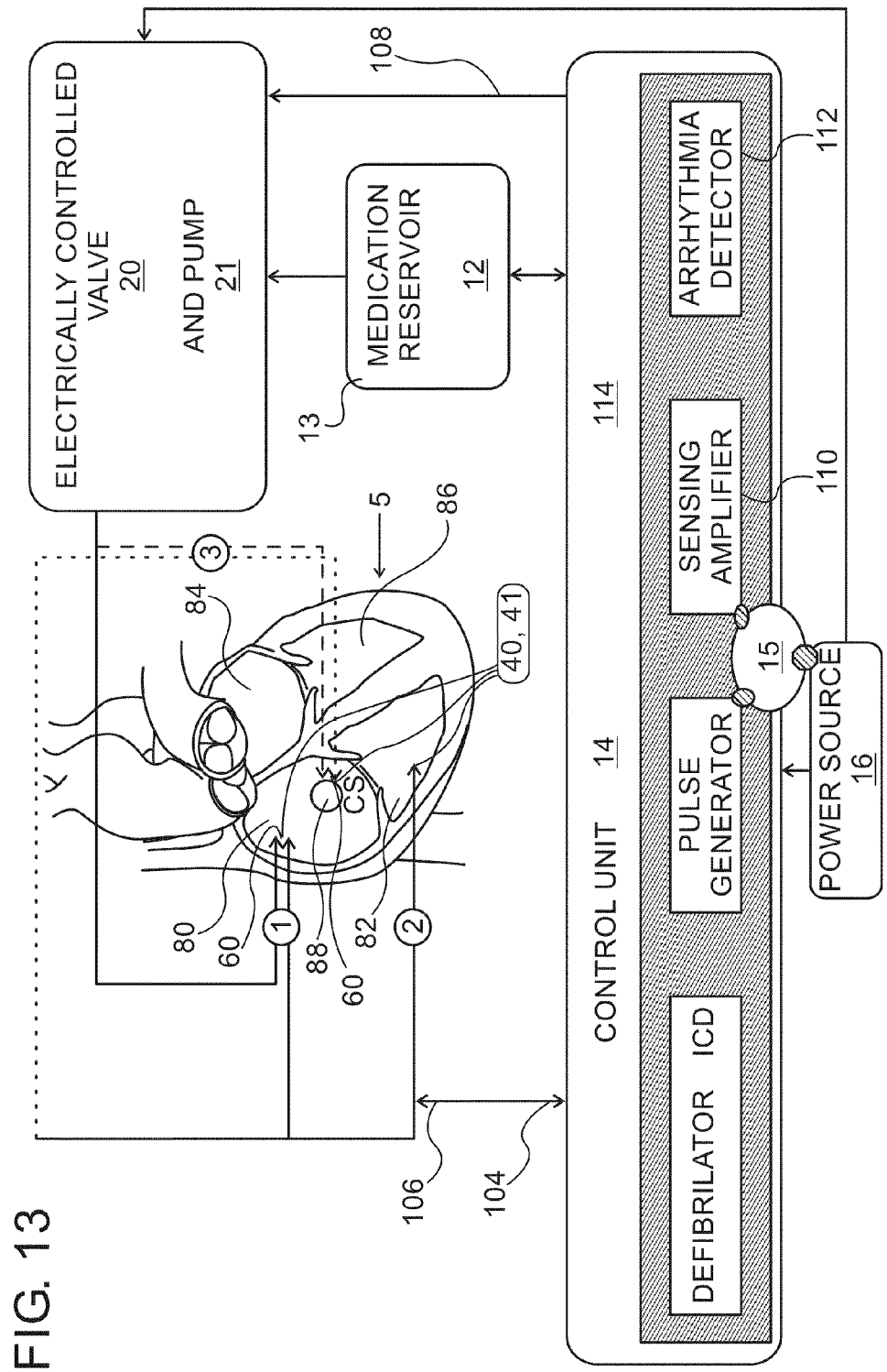
FIG. 13 is a schematic diagram of the cardiac device, in accordance with a preferred embodiment of the present invention.

FIG. 13 schematically illustrates operation of device 10 in a body of a subject.

Control unit 14, powered by power source 16, receives signals (sensing) via sensor 40 and (or) electrode 41, in contact with heart 5, i.e., from right atrium 80, coronary sinus (CS) and right ventricle 82, in the direction of an arrow 104. Control unit 14 then analyzes these signals. The sensing may be performed at various locations of the right side of heart 5, as shown.

In response to the signals, control unit 14 may send electrical signals to heart 5, in the direction of an arrow 106 when operating as a pacemaker 15. The pacing may be performed at various locations of the right side of heart 5 as shown, and defibrillation in right ventricle 82.

Additionally or alternatively, in response to the electrical signals, control unit 14 may operate electrically controlled valve 20, which may include a pump 21, so as to release medication 13 from medication reservoir 12, to heart 5. The release of medication 13 may be to superior vena cava 102, or directly to any location in the right hand side of heart 5 or pulmonary artery.

In order to enable detection of heart arrhythmias, control unit 14 incorporates amplifiers 110 and microprocessor based detectors 112 (e.g., arrhythmia detector), capable of amplifying and processing the signal received from sensor 40. In the case that supraventricular arrhythmia is detected, control unit 14, delivers an electrical signal to the electrically controlled valve 20 and pump 21, initiating the delivery of a medication 13 (e.g., a rapidly hydrolysable cholinergic receptor agonist such as acetylcholine) from medication reservoir 12, to the area of heart 5. If supraventricular arrhythmia persists; one or more additional boluses of medication 13 may be delivered at specified time intervals, which are determined by control unit 14, based on specific algorithms stored therein. Control unit 14 is also programmed to sense the cardiac rate. In the case of bradycardia, whether spontaneous or medication-induced, control unit 14 is responsible of pacing heart 5.

According to the case described by the arrow 1, the electrical contact of electrode 41, is made with right atrium 80.

According to the case described by the arrow 2, the electrical contact of electrode 41, is made with right ventricle 82.

According to the case described by the arrow 3, the electrical contact of electrode 41 is made with the coronary sinus (CS).

Since medication 13 is exhaustible, as is mentioned hereinabove device 10 of the present invention is configured such that reservoir 12 can be replenished with medication 13 without having to remove device 10 from the body.

It will be appreciated that cardiac device 10 of the present invention can be used to treat various pathologies related to abnormal electrical activity of a tissue (heart block, sinus node dysfunction, heart failure and others according to standard indications) and medication 13 is selected according to the specific pathology. For example, treatment of congestive heart failure, pulmonary hypertension and ventricular arrhythmia may be effected using diuretics, vasodilators and antiarrhythmics, respectively. Additionally, other medications, as known, may be used with the cardiac device 10.

It will be appreciated that cardiac device 10 can be implanted in body 7 using methods known in the art for implantation pacemakers and ICDs. It is expected that during the life of this patent many relevant medications, methods, and devices for cardiac treatment will be developed, and the scope of the terms, medication, method, and device for cardiac treatment are intended to include all such new technologies a priori.

As used herein the terms "about" and "substantially" refer to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

RHCA Administration Terminates Atrial Tachycardia

The effect of rapidly hydrolysable cholinergic receptor agonists (RHCA) on supraventricular arrhythmia was tested in anesthetized Wistar rats, as follows.

Experimental Procedures

Induction of atrial tachycardia, atrial fibrillation and atrial flutter in rats—Wistar rats of either sex weighing 450-550 g were used in this study. Rats were anesthetized and atrial tachycardia, atrial fibrillation, or atrial flutter were induced by cardiac stimulation using a programmable stimulator with an isolated constant-current source. Stimuli of rectangular pulses of 2 milliseconds (ms) duration at three times diastolic threshold were delivered via transesophageal bipolar catheter positioned optimally to stimulate the atria. Double and triple extra stimulation techniques or a minimal coupling interval of 10 ms were performed in an attempt to induce atrial arrhythmias. Atrial burst pacing at intervals of 40 to 80 ms was also performed to induce atrial arrhythmias.

Electrocardiogram (ECG) recording—The surface six-lead ECG was continuously recorded from subcutaneous 25-gauge electrodes in each limb of the animal. The ECG channels were amplified (0.1-0.5 mV/cm) and filtered between 0.5-250 Hz. The ECG variables were calculated according to standard criteria.

Rapidly hydrolysable cholinergic receptor agonists (RHCA)—The RHCA were injected either through the tail vein or directly into the right ventricular cavity of rats with induced atrial fibrillation, atrial flutter or atrial tachycardia. The RHCA used in the present study was acetylcholine (ACh). ACh was dissolved at a concentration of either 1 mg/ml or 0.1 mg/ml in 0.9% NaCl solution and was injected either to the tail vein at a dosage of 0.2 mg/kg body weight, or to the right ventricle at a dosage of 0.02 mg/kg body weight.

Experimental Results

Bolus injection of acetylcholine into the tail vein terminated atrial tachycardia within 2-15 seconds and restored normal rhythm within additional 1-5 seconds—Atrial tachycardia was induced as described under experimental procedures hereinabove. FIG. 2a illustrates a representative ECG recording from a single rat with induced atrial tachycardia. The analysis of three standard ECG leads recording (I, II and III in FIG. 2a) shows that there exists a well-organized atrial tachycardia with AV conduction 4:1, P-P intervals (i.e., the intervals between two P waves) of 71±2 milliseconds (ms) [844 beats per minute (bpm)] and R-R intervals (i.e., the intervals between two R waves) of 284±3 ms (211 bpm). The episodes of atrial tachycardia in rats lasted, on average, for 7.6±1.8 minutes (n=30) upon induction. Bolus injection of 0.1 ml of 1 mg/ml acetylcholine (dosage 0.2 mg/kg body weight) via the tail vein terminated the arrhythmia with a lag of 2.6 seconds (FIG. 2a). The P-P and R-R intervals immediately following the RHCA administration were moderately prolonged (650±3 ms and 652±3 ms, respectively); the sinus rhythms gradually accelerated and reached its pre-arrhythmic value within about 1 minute following RHCA administration (not shown). All ten rats tested were successfully converted to sinus rhythm within 2-5 seconds following RHCA (0.02-0.2 mg/kg body weigh) injection via the tail vein.

Bolus injection of acetylcholine into the right ventricular cavity terminated atrial tachycardia within 0.5-10.5 seconds and restored normal rhythm within additional 1-5 seconds—FIG. 2b shows an example of termination of a high-frequency, well-organized atrial tachycardia by RHCA injection into the right ventricular cavity. As is shown in FIG. 2b, following 0.5 s from the administration of a bolus injection of 0.1 ml of 0.1 mg/ml acetylcholine (dosage 0.02 mg/kg body weight), the atrial tachycardia was terminated. After short period (1.25 s) of cardiac arrest two escape nodal beats appeared and the sinus node activity recovered (appeared P-waves) with high degrees of AV block. Following about 4.5 sec the AV conduction completely recovered. It should be emphasize that following acetylcholine hydrolysis, the AV node conduction appeared as high degree AV block (2.5 seconds) and completely recovered after a short period (at about 6 seconds following RHCA administration). Thus, RHCA administration resulted in very short periods of cardiac arrest, escape rhythm, high degree AV block, then $1^{st}$ degree AV bock and sinus bradycardia which all disappear within 15 seconds (not shown). All twelve rats tested were successfully converted to sinus rhythm following RHCA (0.02-0.4 mg/kg body weight) injection into the right ventricle.

Atrial flutter was induced as described under experimental procedures hereinabove. The episodes of atrial flutter in rats lasted, on average, for 6.8±2.4 minutes (n=9) upon induction. All nine rats tested were converted to sinus rhythm within 2-5 seconds following RHCA (0.02-0.3 mg/kg body weigh) injection via the tail vein; all eight rats tested were converted to sinus rhythm following RHCA (0.02-0.2 mg/kg body weight) injection into the right ventricle.

Altogether, these results demonstrate, for the first time, that a single dose administration of an RHCA such as acetylcholine can terminate atrial tachycardia, as well atrial flutter and convert the heart to normal sinus rhythm. These results therefore suggest the use of RHCA in treating atrial tachycardia and atrial flutter.

Example 2

RHCA Administration Terminates Atrial Fibrillation

Atrial fibrillation was elicited in rats as described in Example 1, hereinabove.

Experimental Results

Bolus injection of acetylcholine into the right ventricular cavity terminated atrial fibrillation within 0.5-10.5 seconds and restored normal rhythm within additional 1-5 seconds—FIGS. 3a-b illustrate ECG recordings of a rat undergoing atrial fibrillation from the three standard leads (I, II, and III) and the suppression of atrial fibrillation by RHCA administration via the right ventricular cavity. Atrial fibrillation was characterized by variable f-f intervals (range 48-62 ms, 970-1250 bpm) and RR intervals (range 100-420 ms, 140-600 bpm). The average duration of such atrial fibrillation episodes without any further treatment (i.e., the time interval since induction till spontaneous termination) was 8.6±2.2 minutes (n=32). Bolus injection of 0.1 ml of 0.2 mg/ml acetylcholine (dosage 0.04 mg/kg body weight) into the right ventricular cavity converted the atrial fibrillation to sinus rhythm within 1.5 seconds; transient sinus bradycardia and AV block were maximal immediately following the injection and disappeared within 20 seconds (not shown).

Figure 4:
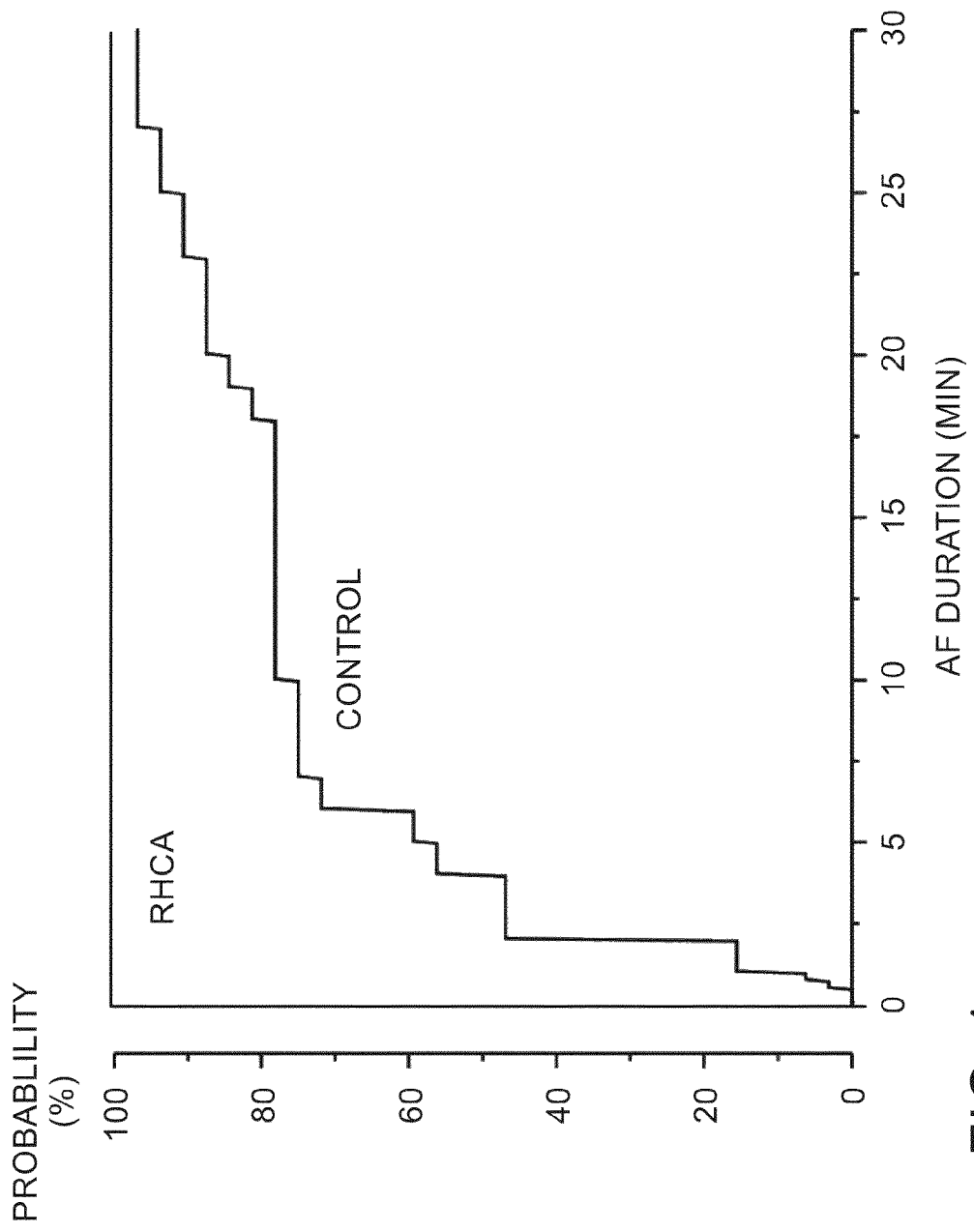
FIG. 4—is a graph illustrating the probability density of the atrial fibrillation episode duration in control rats (n=32) and in rats treated with a bolus injection of RHCA in the right ventricular cavity (n=10). Note that while median duration of the atrial fibrillation episode in control rats was longer than 4 minutes, the RHCA application terminated the arrhythmia within few seconds.

Further statistical analysis of the probability density of atrial fibrillation termination revealed that while 100% of the atrial fibrillation cases are terminated within 8.4±1.9 seconds using RHCA administration (n=10). The episodes of atrial fibrillation in the untreated rats (n=32) are terminated spontaneously within 8.6±2.2 minutes and are significantly longer than treated (Kholmogorov-Smirnov test, $p<0.05$; FIG. 4).

These results demonstrate that atrial fibrillation can be terminated immediately using a bolus injection of acetylcholine into the right ventricular cavity.

Figure 5:
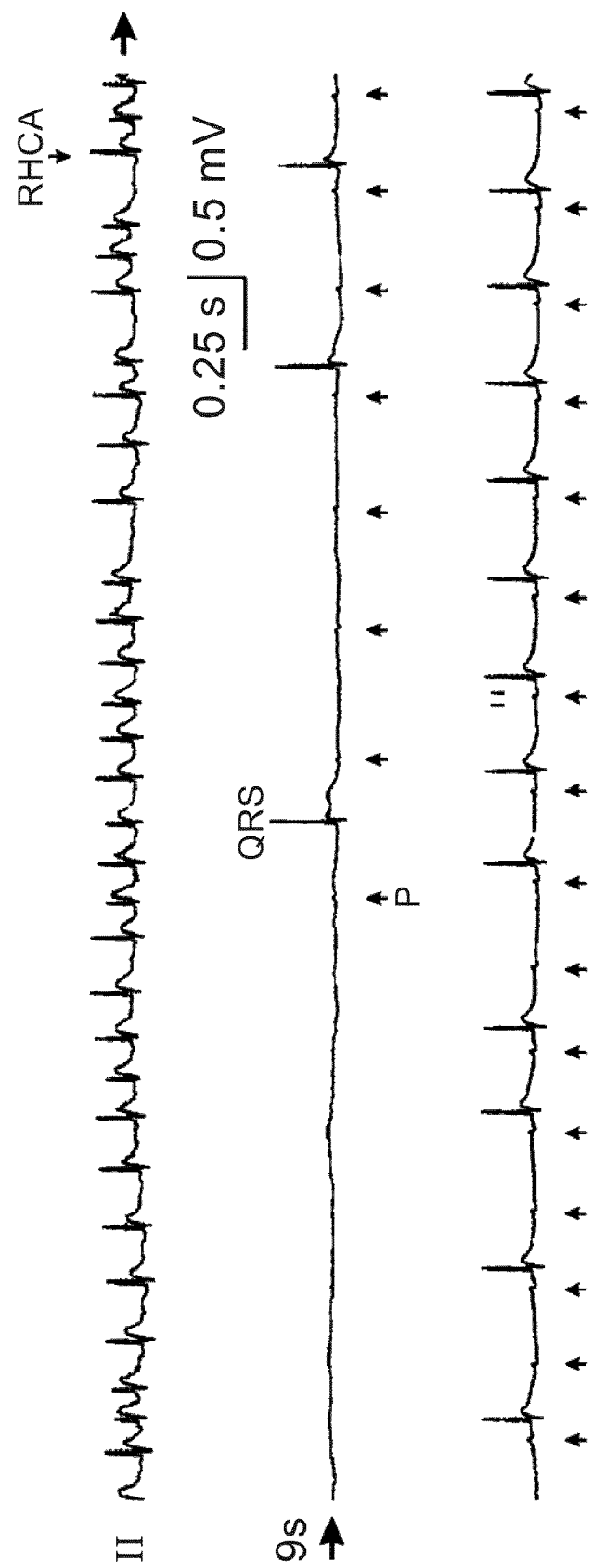
FIG. 5—illustrates ECG recording of a rat after the induction of atrial fibrillation and the termination of atrial fibrillation following the administration of RHCA via the tail vein. Shown is recording from the standard lead II over a time scale. Note the variable f-f and R-R intervals characterizing atrial fibrillation. Also note that a bolus injection of 0.1 ml of 1 mg/ml acetylcholine (dosage 0.2 mg/kg body weight) through the tail vein terminated the arrhythmia within 9.8 seconds and introduced a very short period of cardiac arrest, nodal escape rhythm and various degrees of AV block. Following the additional 1.5 seconds, the AV conduction recovered.

Bolus injection of acetylcholine into the tail vein terminated atrial fibrillation within 2-15 seconds and restored normal rhythm within additional 1-5 seconds—FIG. 5 illustrates ECG recording of atrial fibrillation. Bolus administration of 0.1 ml of 1 mg/ml acetylcholine (dosage 0.2 mg/kg body weight) through the vein tail terminated the arrhythmia within 9.8 seconds, introduced very short periods of cardiac arrest, escape rhythm and various degrees of AV block. Following the additional 1.5 seconds, the SA and AV nodes recovered.

Figure 6:
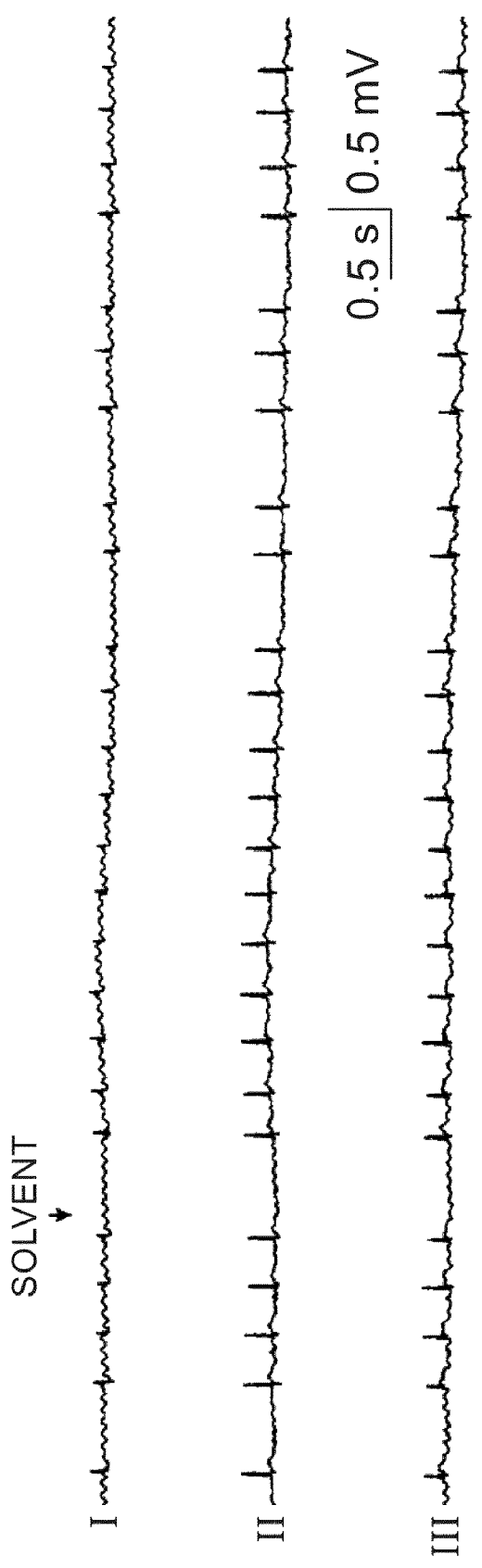
FIG. 6—illustrates ECG recording of a rat after the induction of atrial fibrillation and the lack of effect of saline administration via the ventricular cavity on the duration or characteristic of atrial fibrillation episode.

FIG. 6 illustrates ECG recordings of a rat undergoing atrial fibrillation and the lack of effect of saline administration (0.9% NaCl) via the right ventricular cavity on the duration or characteristic of atrial fibrillation. Similar results were observed in 9 and 6 additional rats which were injected with 0.9% NaCl into the ventricular cavity or the tail vein, respectively. These results demonstrate that the solvent used for dissolving acetylcholine (i.e., 0.9% NaCl) has no effect on atrial fibrillation termination.

Altogether, these results demonstrate that acetylcholine is capable of terminating atrial fibrillation and converting the heart into sinus rhythms within seconds following its administration. These results suggest the use of RHCA to terminate atrial fibrillation by either intraventricular or intravenous injection.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

U.S. Pat. No. 4,978,338 to Melsky et al., entitled "Implantable infusion apparatus", Dec. 18, 1990

U.S. Pat. No. 5,575,770 to Melsky et al., entitled "Implantable drug infusion system with safe bolus capability", Nov. 19, 1996

U.S. Pat. No. 5,736,528 to Belardinelli et al., entitled "N.sup.6-(epoxynorborn-2-yl)adenosines as A.sub.1 adenosine receptor agonists", April 1998

U.S. Patent Application 20030032998 to Altman, entitled "Cardiac drug delivery system and method for use", February 2003

U.S. Patent Application 20030130616 to Steil and Rebrin, entitled "Closed loop system for controlling insulin infusion", Jul. 10, 2003

U.S. Pat. No. 6,537,974 to Wolff, entitled "Method of treating arrhythmias", March 2003

U.S. Pat. No. 6,635,049 to Robinson et al., entitled "Drug bolus delivery system", Oct. 21, 2003

U.S. Pat. No. 6,716,196 to Lesh et al., entitled "Catheter system for delivery of therapeutic compounds to cardiac tissue", Apr. 6, 2004

Arnsdorf M F (1989) Cardiac excitability and antiarrhythmic drugs: a different perspective. J Clin Pharmacol 29:395-404.

Boyett M R, Kirby M S, Orchard C H, Roberts A (1988) The negative inotropic effect of acetylcholine on ferret ventricular myocardium. J Physiol 404:613-635.

Bunemann M, Pott L (1995) Down-regulation of A1 adenosine receptors coupled to muscarinic K+ current in cultured guinea-pig atrial myocytes. J Physiol 482:81-92.

Chiou C W, Eble J N, Zipes D P (1997) Efferent vagal innervation of the canine atria and sinus and atrioventricular nodes. The third fat pad. Circulation 95:2573-2584.

Cohn A E (1912) Auricular tachycardia with a consideration of certain differences between the two vagi. Journal of Experimental Medicine 15:49-62.

Dascal N, Schreibmayer W, Lim N F, et al. (1993) Atrial G protein-activated K+ channel: expression cloning and molecular properties. Proc Natl Acad Sci USA 90:10235-10239.

Dobrev D, Graf E, Wettwer E, et al. (2001) Molecular basis of downregulation of G-protein-coupled inward rectifying K(+) current (I(K,ACh) in chronic human atrial fibrillation: decrease in GIRK4 mRNA correlates with reduced I(K,ACh) and muscarinic receptor-mediated shortening of action potentials. Circulation 104:2551-2557.

Dobrzynski H, Janvier N C, Leach R, et al. (2002) Effects of ACh and adenosine mediated by Kir3.1 and Kir3.4 on ferret ventricular cells. Am J Physiol Heart Circ Physiol 283:H615-630.

Dobrzynski H, Marples D D, Musa H, et al. (2001) Distribution of the muscarinic K+ channel proteins Kir3.1 and Kir3.4 in the ventricle, atrium, and sinoatrial node of heart. J Histochem Cytochem 49:1221-1234.

Fuster V, Ryden L E, Asinger R W, et al. (2001) ACC/AHA/ESC guidelines for the management of patients with atrial fibrillation: executive summary. J Am Coll Cardiol 38:1231-1266.

Hartzell H C (1979) Adenosine receptors in frog sinus venosus: slow inhibitory potentials produced by adenine compounds and acetylcholine. J Physiol 293:23-49.

Kabell G, Buchanan L V, Gibson J K, Belardinelli L (1994) Effects of adenosine on atrial refractoriness and arrhythmias. Cardiovasc Res 28:1385-1389.

Kawano H, Okada R, Yano K (2003) Histological study on the distribution of autonomic nerves in the human heart. Heart Vessels 18:32-39.

Kennedy M E, Nemec J, Corey S, Wickman K, Clapham D E (1999) GIRK4 confers appropriate processing and cell surface localization to G-protein-gated potassium channels. J Biol Chem 274:2571-2582.

Koumi S, Wasserstrom J A (1994) Acetylcholine-sensitive muscarinic K+ channels in mammalian ventricular myocytes. Am J Physiol 266:H1812-1821.

Kovoor P, Wickman K, Maguire C T, et al. (2001) Evaluation of the role of I(KACh) in atrial fibrillation using a mouse knockout model. J Am Coll Cardiol 37:2136-2143.

Krapivinsky G, Gordon E A, Wickman K, et al. (1995) The G-protein-gated atrial K+ channel IKACh is a heteromultimer of two inwardly rectifying K(+)-channel proteins. Nature 374:135-141.

Kubo Y, Reuveny E, Slesinger P A, et al. (1993) Primary structure and functional expression of a rat G-protein-coupled muscarinic potassium channel. Nature 364:802-806.

Kurachi Y, Nakajima T, Sugimoto T (1986) On the mechanism of activation of muscarinic K+ channels by adenosine in isolated atrial cells: involvement of GTP-binding proteins. Pflugers Arch 407:264-274.

Logothetis D E, Kurachi Y, Galper J, et al. (1987) The beta gamma subunits of GTP-binding proteins activate the muscarinic K+ channel in heart. Nature 325:321-326.

McMorn S O, Harrison S M, Zang W J, et al. (1993) A direct negative inotropic effect of acetylcholine on rat ventricular myocytes. Am J Physiol 265:H1393-1400.

Moe G K, Abildskov J A (1959) Atrial fibrillation as a self-sustaining arrhythmia independent of focal discharge. Am Heart J 58:59-70.

North R A (1989) Twelfth Gaddum memorial lecture. Drug receptors and the inhibition of nerve cells. Br J Pharmacol 98:13-28.

Ovsyshcher I E, Barold S S (2004) Drug-Induced Bradycardia: To Pace or Not to Pace? Pacing Clin Electrophysiol. 27:1144-7.

Prystowsky E N, Benson D W, Jr., Fuster V, et al. (1996) Management of patients with atrial fibrillation. A Statement for Healthcare Professionals. From the Subcommittee on Electrocardiography and Electrophysiology, American Heart Association. Circulation 93:1262-1277.

Schram G, Pourrier M, Melnyk P, Nattel S (2002) Differential distribution of cardiac ion channel expression as a basis for regional specialization in electrical function. Circ Res 90:939-950.

Takano M, Noma A (1997) Development of muscarinic potassium current in fetal and neonatal rat heart. Am J Physiol 272:H1188-1195.

Tse H F, Lau C P (2003) Does sinus rhythm beget sinus rhythm? Effects of prompt cardioversion on the frequency and persistence of recurrent atrial fibrillation. Card Electrophysiol Rev 7:359-365.

Waldo A L (2003) Mechanisms of atrial fibrillation. J Cardiovasc Electrophysiol 14:S267-274.

Wellens H J (2000) Pulmonary vein ablation in atrial fibrillation: hype or hope? Circulation 102:2562-2564.

Wellner-Kienitz M C, Bender K, Meyer T, Bunemann M, Pott L (2000) Overexpressed A(1) adenosine receptors reduce activation of acetylcholine-sensitive K(+) current by native muscarinic M(2) receptors in rat atrial myocytes. Circ Res 86:643-648.

Wickman K, Krapivinsky G, Corey S, et al. (1999) Structure, G protein activation, and functional relevance of the cardiac G protein-gated K+ channel, IKACh. Ann N Y Acad Sci 868:386-398.

Wyse D G, Gersh B J (2004). Atrial Fibrillation: A Perspective Thinking Inside and Outside the Box. Circulation. 2004; 109:3089-3095.

Yang Z K, Boyett M R, Janvier N C, et al. (1996) Regional differences in the negative inotropic effect of acetylcholine within the canine ventricle. J Physiol 492:789-806.

Zemlin C, Mironov S, Pertsov A (2003) Delayed success in termination of three-dimensional reentry: role of surface polarization. J. Cardiovasc Electrophysiol 14:S257-263.

What is claimed is:

1. A method of treating supraventricular arrhythmias (SVA) in a subject in need thereof, the method comprising: administering to the subject a bolus injection of 0.001-20 mg per KG body weight of acetylcholine or an acetylcholine salt which has the ability to transiently modulate at least one electrical property of at least a portion of atrial cells thereby treating the supraventricular arrhythmia in the subject.

2. The method of claim 1, wherein said SVA is atrial fibrillation.

3. The method of claim 1, wherein said SVA is atrial tachycardia.

4. The method of claim 1, wherein said SVA is atrial flutter.

5. The method of claim 1, wherein said acetylcholine or acetylcholine salt is formulated for intravascular, intramuscular and/or intracardiac administration.

6. The method of claim 5, wherein said intracardiac administration is into a chamber of a heart.

7. The method of claim 5, wherein said intracardiac administration is effected via the right atrium, left atrium, right ventricle, and/or left ventricle.

8. The method of claim 5, wherein said intravascular administration is effected via a vein and/or an artery.

9. The method of claim 8, wherein said artery is a coronary artery and/or a pulmonary artery.

10. The method of claim 8, wherein said vein is a peripheral vein, a central vein and/or a coronary sinus.

11. The method of claim 10, wherein said central vein is a superior vena cava and/or an inferior vena cava.

12. The method of claim 1, wherein said administration is effected using a catheter, a cannula, a needle, syringe and/or a pump.

13. The method of claim 12, wherein said catheter is a part of a pacing lead-catheter.

14. The method of claim 12, wherein said catheter comprises a lumen for drug delivery.

15. The method of claim 1, wherein said acetylcholine salt is selected from the group consisting of acetylcholine chloride, acetylcholine bromide, acetylcholine iodide.

16. The method of claim 1, wherein said bolus injection of acetylcholine or acetylcholine salt is from a range of 0.02-0.4 mg per kg body weight.

17. The method of claim 1, wherein said acetylcholine or acetylcholine salt is incapable of modulating at least one electrical property of ventricular cells.

18. The method of claim 1, wherein said at least one electrical property is selected from the group consisting of refractoriness, excitability, speed of excitation propagation, focal automaticity, and spatial pattern of excitation.

19. The method of claim 1, wherein said acetylcholine or acetylcholine salt has the ability to transiently modulate said at least one electrical property of said at least a portion of atrial cells for no more than 5 seconds.

20. The method of claim 1 wherein said cholinergic receptor is a muscarinic m2 receptor.

21. The method according to claim 1 wherein the quantity of said acetylcholine or acetylcholine salt in said bolus is such that the concentration acetylcholine or acetylcholine salt in the blood after injection will fall to near zero in seconds, thereby avoiding the proarrhythmic effects of the acetylcholine or acetylcholine salt.

* * * * *